(12) United States Patent
Denham et al.

(10) Patent No.: US 11,633,197 B2
(45) Date of Patent: Apr. 25, 2023

(54) BONE CUT GUIDE APPARATUS AND METHOD

(71) Applicant: NEXTREMITY SOLUTIONS, INC., Warsaw, IN (US)

(72) Inventors: Greg Denham, Warsaw, IN (US); Ryan Schlotterback, Warsaw, IN (US); Daren Granger, Warsaw, IN (US)

(73) Assignee: Medartis AG, Basel (CH)

( * ) Notice: Subject to any disclaimer, the term of this patent is extended or adjusted under 35 U.S.C. 154(b) by 65 days.

(21) Appl. No.: 17/205,461

(22) Filed: Mar. 18, 2021

(65) Prior Publication Data

US 2021/0290250 A1    Sep. 23, 2021

Related U.S. Application Data

(60) Provisional application No. 62/991,879, filed on Mar. 19, 2020.

(51) Int. Cl.
| | | |
|---|---|---|
| *A61B 17/15* | (2006.01) | |
| *A61B 17/17* | (2006.01) | |
| *A61B 17/56* | (2006.01) | |

(52) U.S. Cl.
CPC .......... *A61B 17/1775* (2016.11); *A61B 17/15* (2013.01); *A61B 17/151* (2013.01); *A61B 17/1796* (2013.01); *A61B 2017/564* (2013.01)

(58) Field of Classification Search
CPC .... A61B 17/1775; A61B 17/15; A61B 17/151
See application file for complete search history.

(56) References Cited

U.S. PATENT DOCUMENTS

| | | |
|---|---|---|
| 5,042,983 A | 8/1991 | Rayhack |
| 2016/0235414 A1 | 8/2016 | Hatch et al. |
| 2017/0014143 A1 | 1/2017 | Dayton et al. |
| 2017/0079669 A1 | 3/2017 | Bays et al. |
| 2018/0110530 A1 | 4/2018 | Wagner et al. |
| 2019/0357919 A1 | 11/2019 | Fallin et al. |
| 2020/0060690 A1 * | 2/2020 | Woodard ............... A61B 17/15 |

FOREIGN PATENT DOCUMENTS

| | | | |
|---|---|---|---|
| EP | 1508316 A1 | 2/2005 | |
| GB | 2583572 A | 11/2020 | |
| WO | 2019113394 A1 | 6/2019 | |
| WO | WO-2019113394 A1 * | 6/2019 | ............. A61B 17/15 |

OTHER PUBLICATIONS

UKIPO Search Report dated Oct. 21, 2021.
UKIPO Search Report dated Feb. 23, 2021.

* cited by examiner

*Primary Examiner* — Christian A Sevilla
(74) *Attorney, Agent, or Firm* — Heslin Rothenberg Farley & Mesiti P.C.; Victor A. Cardona, Esq.

(57) ABSTRACT

A bone cut guide includes a stem having a stem longitudinal axis and an anchoring portion proximal to the stem and connected to the stem by a cut body. The anchoring portion includes an anchoring opening configured to receive a wire therethrough to connect the anchoring portion to a bone. The cut body includes a cut slot configured to receive a saw to cut the bone.

8 Claims, 34 Drawing Sheets

BONE CUT GUIDE APPARATUS AND METHOD

CROSS-REFERENCE TO RELATED APPLICATIONS

The present application claims priority to U.S. Provisional Application Ser. No. 62/991,879 filed on Mar. 19, 2020, which is incorporated herein by reference in its entirety.

The present application is related to U.S. application Ser. No. 17/022,761 filed Sep. 16, 2020, which claims the benefit of U.S. Provisional Application Ser. No. 62/900,920 filed Sep. 16, 2019, each of which are incorporated herein by reference in their entireties.

BACKGROUND

Field of the Invention

This application relates to apparatuses, devices, and methods for adjusting and joining bones.

Description of the Related Art

There are various procedures that involve cutting, altering and moving bone pieces. Thus, a need exists for alternative designs for joining two bone pieces, including systems and methods that allow adjustment of the angle of flexion between the two bones.

SUMMARY

The present invention provides, in a first aspect, a bone cut guide which includes a stem having a stem longitudinal axis and an anchoring portion proximal to the stem and connected to the stem by a cut body. The anchoring portion includes an anchoring opening configured to receive a wire therethrough to connect the anchoring portion to a bone. The cut body includes a cut slot configured to receive a saw to cut the bone.

The present invention provides, in a second aspect, a method for use in aligning bones which includes attaching a first portion of a bone cut guide to a first bone by receiving a first wire in a first opening of the first portion of the bone cut guide. The bone cut guide is located in a first position relative to the first bone and a second bone and a first cut is made of the first bone through a slot of the bone cut guide. The bone cut guide is located in a second position relative to the first bone and the second bone and a second cut is made of the first bone or the second bone. The first bone is aligned with the second bone in a desired final position.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Figure 1:
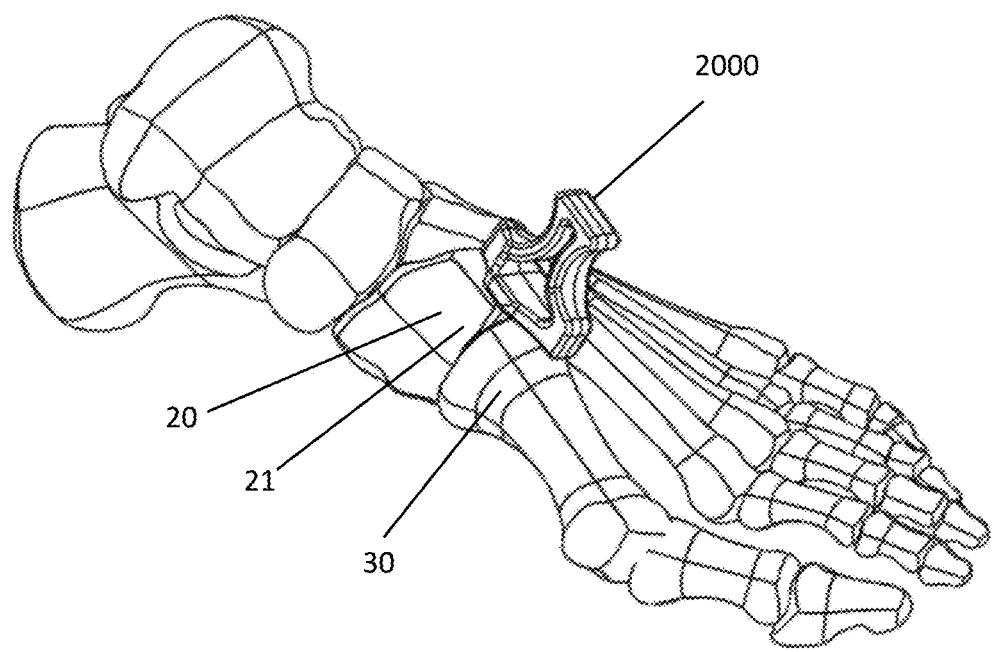
FIG. 1 is a front perspective view of a post drill guide engaged with a foot in accordance with an aspect of the present invention.
Figure 2:
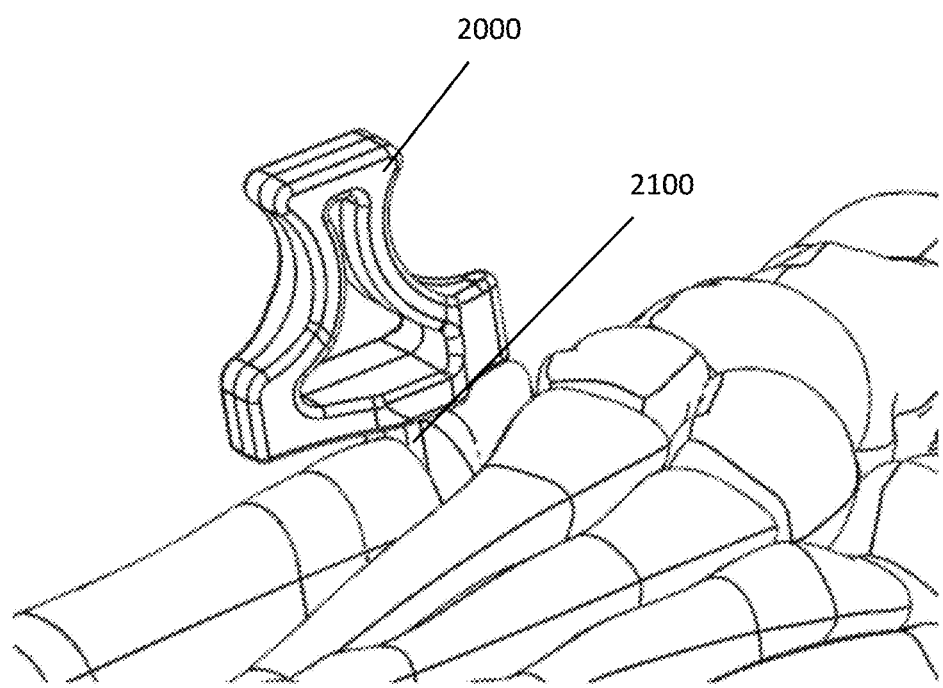
FIG. 2 is a side perspective view of the post drill guide of FIG. 1.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for cutting tools for orthopedic surgery involving a foot or lower extremities. However, those possessing an ordinary level of skill in the relevant art will appreciate that other extremities, joints, and parts of the musculoskeletal system are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present invention may be applied to any orthopedic surgery, such as on the hand as well as other upper and lower extremities and may be implemented in other treatments sites that have similar anatomical considerations.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As will be described below, the present invention includes systems and methods for correcting a deformity of the human foot.

As depicted in FIGS. 1-4 and 34-35, a post drill guide 2000 may be engaged with a foot 10 (i.e., after appropriate surgical preparation) such that a paddle 2100 thereof is located in an articular space between a medial cuneiform 20 and a first metatarsal 30 of foot 10. Guide 2000 also includes a bore 2300 for receiving a K-wire 2400 (e.g., a 2 mm K-wire) therethrough from a top side thereof toward a bottom side thereof adjacent foot 10. Drill guide 2000 may include gripping portions 2010 and paddle 2100 may be located longitudinally offset from a longitudinal center 2015 of guide 2000 relative to a longitudinal dimension of a bottom side 2035 of drill guide 2000. A cavity 2020 may be bounded by inner surfaces of gripping portions 2010.

Figure 3:
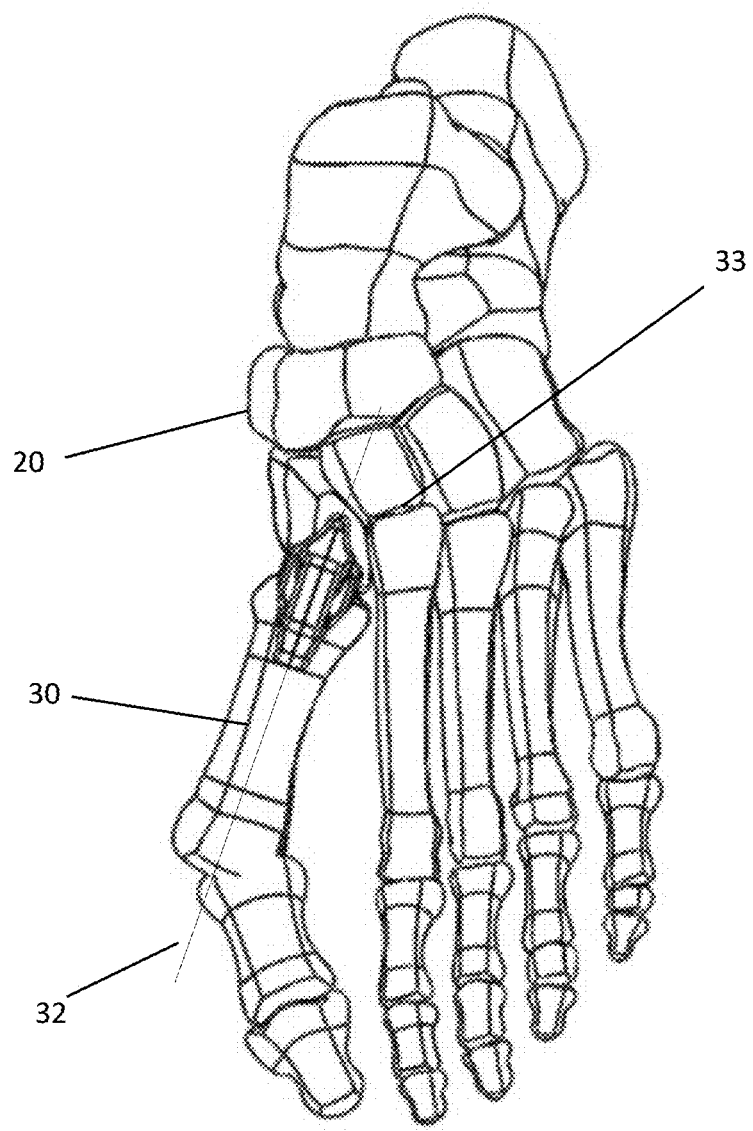
FIG. 3 is a top view of the post drill guide and foot of FIG. 1.
Figure 4:
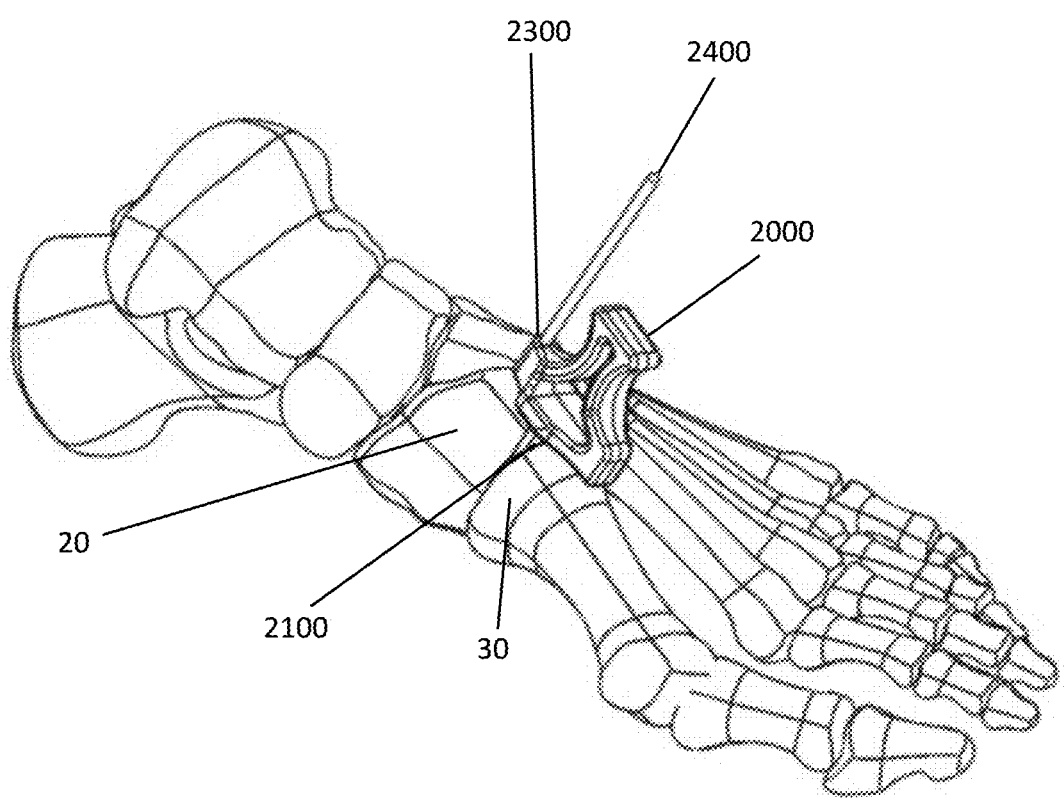
FIG. 4 is a perspective view of the post drill guide and foot of FIG. 1 with a K-wire received through the post drill guide into the foot.

As depicted in FIG. 3, a longitudinal dimension of bottom side 2035 of drill guide 2000 may be aligned with, or substantially parallel to, a longitudinal axis 32 of first metatarsal 30. For example, K-wire 2400 may be loosely placed into bore 2300 of Post Drill Guide 2000 to allow an angle of the K-Wire to be observed to determine if the K-wire is both parallel to a tarsal-metatarsal (TMT) joint 33 and in a middle of a long axis of medial cuneiform 20. For example, the K-wire may generally be placed dorsal-lateral to plantar medial. The K-wire may be adjusted to allow such alignment and then the K-wire may be inserted through bore 2300 of post drill guide 2000 into foot 10 as depicted in FIG. 4. The placement of the K-wire, as described, establishes a reference point for a procedure for correcting a deformity of foot 10 and establishes a primary plane between the two bones.

Figure 5:
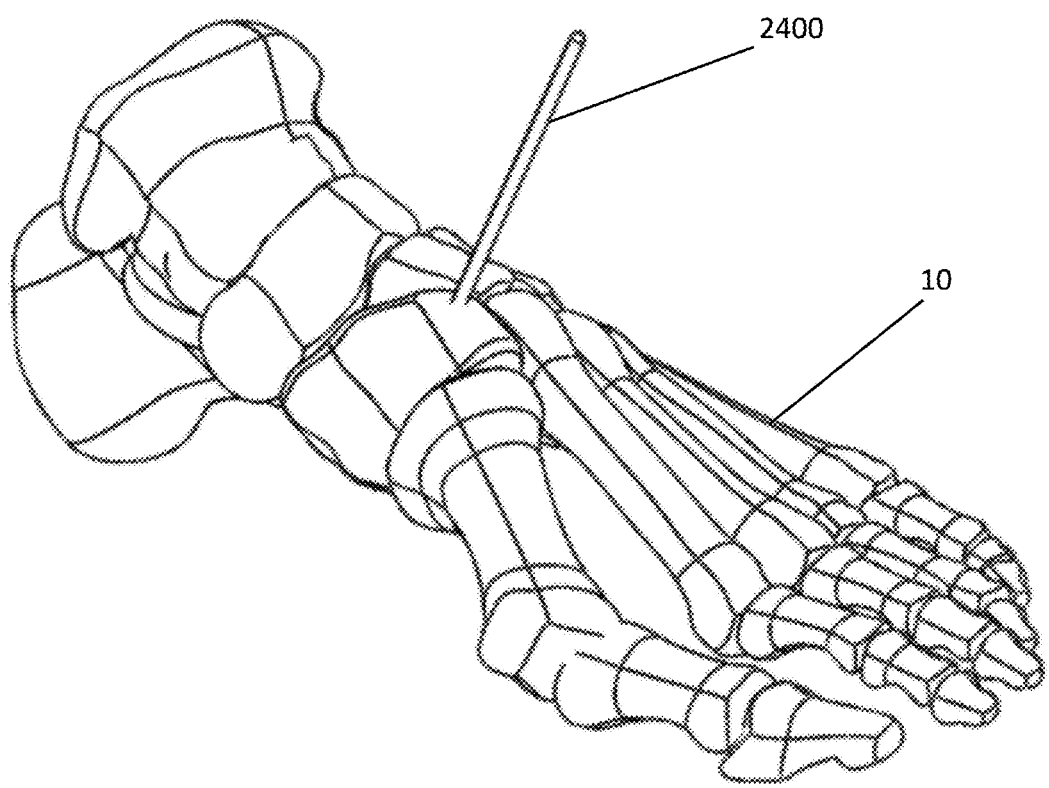
FIG. 5 is a front perspective view of the foot and K-wire of FIG. 4 with the post drill guide removed.
Figure 6:
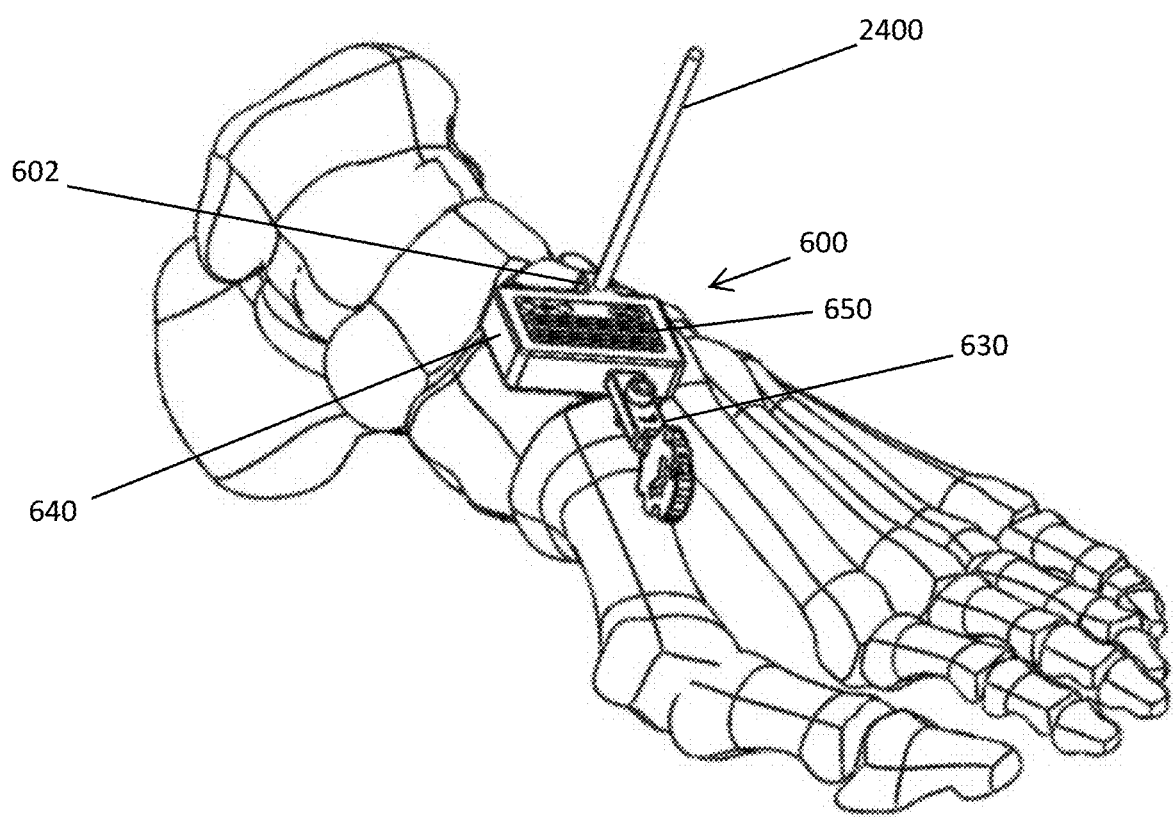
FIG. 6 is a front perspective view of the foot and K-wire of FIG. 5 with a cut guide received on the K-wire.
Figure 7:
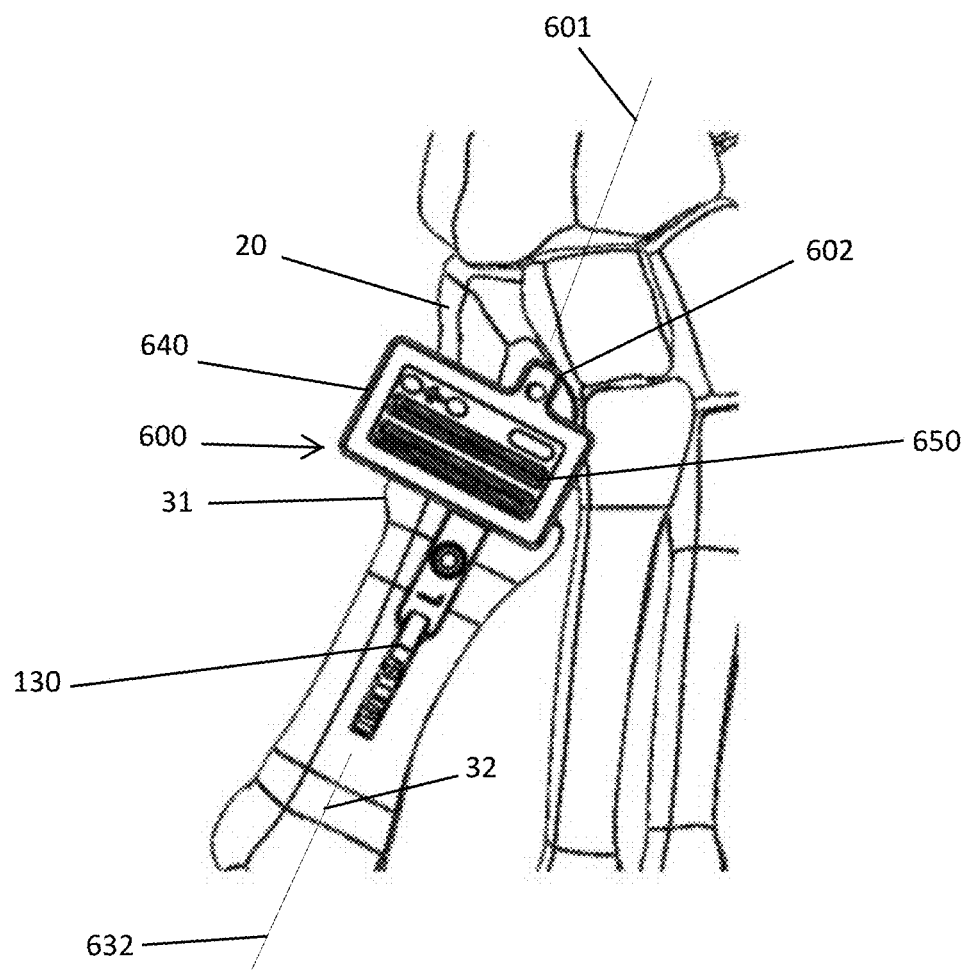
FIG. 7 is a top view of the cut guide and a portion of the foot of FIG. 6.

As depicted in FIG. 5, the surgeon may remove post drill guide 2000, leaving K-wire 2400 in the bone (i.e., foot 10). A cut guide 600 may be placed over K-wire 2400 via an anchoring hole 610 (FIG. 10) extending vertically through cut guide 600 receiving the K-wire. As depicted in FIGS. 6-7, a stem 630 of cut guide 600 is connected to a cut body 640 thereof and has a longitudinal dimension or axis 632 aligned with or extending parallel to axis 32 of first metatarsal 30.

Cut guide 600 may include multiple slots 650 (e.g., 4) for receiving a saw blade (e.g., a saw 170) to allow a cut of a bone (e.g., cuneiform 20) attached to cut guide 600 or a bone (e.g., first metatarsal 30) coupled to such cut guide. Slots 650 may have longitudinal dimensions about, or at least approximately, perpendicular to a longitudinal dimension of a stem 630 of cut guide 600.

Figure 8:
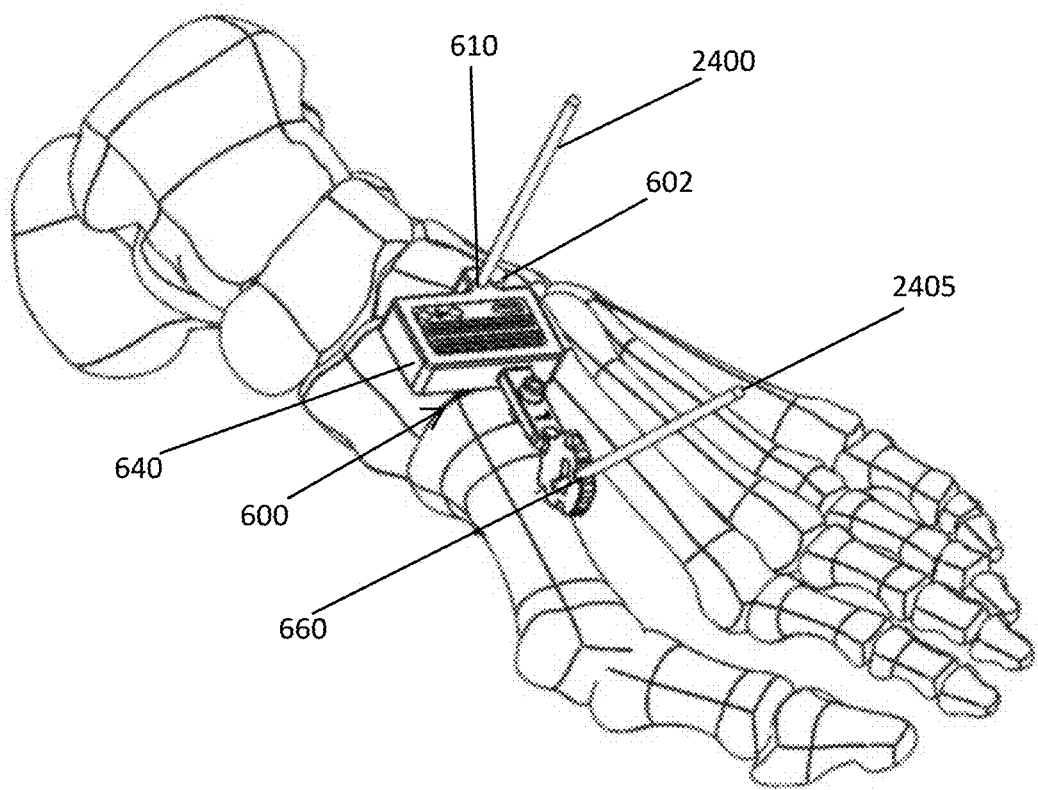
FIG. 8 is a front perspective view of the foot and cut guide of FIG. 7 with a second K-wire received through a distal hole of the cut guide.

A proximal anchoring portion 602 may extend proximally away from stem 130 and may have a longitudinal axis 601 aligned with longitudinal axis 132 of stem 130. Anchoring portion 602 may include and have interior surfaces bounding anchoring hole 610 extending vertically therethrough from a top side thereof toward foot 10 as depicted in FIGS. 7-8, for example.

Figure 9:
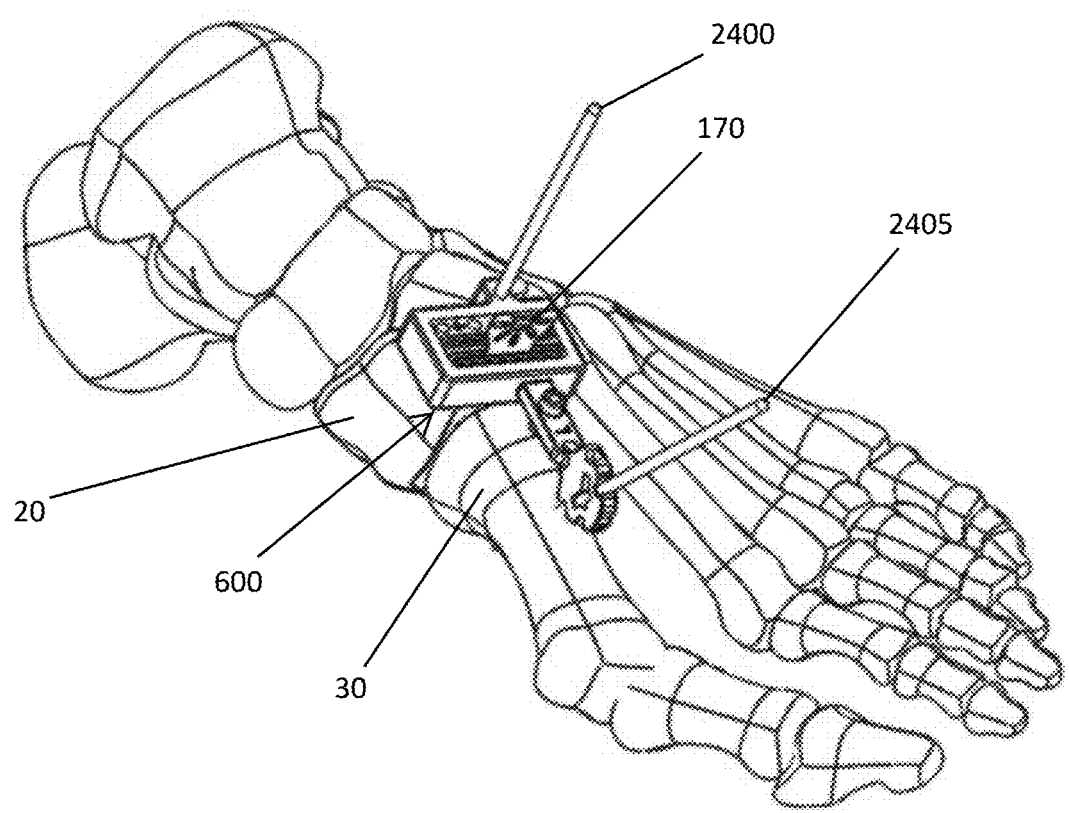
FIG. 9 is a front perspective view of the cut guide received on the foot of FIG. 8 with a saw blade received in a slot of the cut guide.
Figure 10:
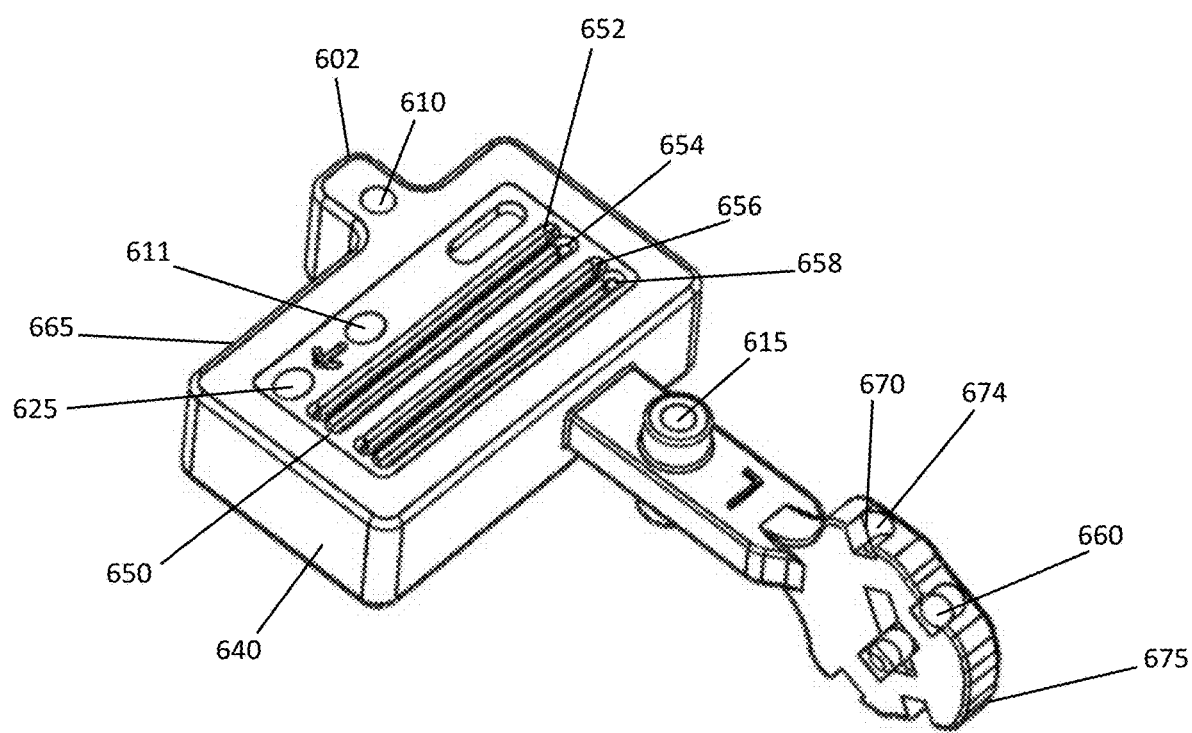
FIG. 10 depicts a top perspective view of the cut guide of FIG. 6.

As depicted in FIGS. 7-10, a K-wire 2405 (e.g., a 2 mm K-wire), similar to K-wire 2400, may be inserted through a distal locking hole 660 in stem 630 into bone (i.e., foot 10) to pin the cut guide in place such that a proximal end 31 of the metatarsal may be immobilized relative to cuneiform 20. Distal locking hole 660 may be aligned at a non-perpendicular angle relative to a longitudinal dimension of stem 630 as depicted in FIGS. 9-10. For example, a top end of the K-wire received in locking hole 660 may be located further distally than a bottom end thereof such that the top portion is angled away from K-wire 2400 and/or anchoring portion 200 to securely fasten cut guide 100 relative to first metatarsal 30. Such alignment of distal locking hole 660 and insertion of K-wire 2400 therethrough into a bone (e.g., into first metatarsal 30) at an angle greater than or less than perpendicular may allow a frictional force to be applied on K-wire 2400 in a longitudinal direction relative to axis 632 to further inhibit movement and secure K-wire 2400 and stem 630 to the bone compared to a perpendicular or approximately perpendicular locking hole. In another example, such a perpendicular or approximately perpendicular locking hole may be utilized in place of distal locking hole 660.

As described above, an axis of locking hole 660 may be aligned relative to a longitudinal dimension of stem 630 at an angle greater than or less than perpendicular. Further, additional locking holes 670 may be located on a proximal end 665 of cut guide 600 or on a distal end 675 of stem 630 to fix cut guide 600 in a particular position as described above relative to locking hole 660. Such additional locking holes may be oriented at various angles relative to an axis of stem 630. For example, a top end of a K-wire may be received in a distal locking hole 674 of locking holes 670 angled away from a bottom thereof such that the top end is more proximal than the bottom (i.e., opposite to an alignment described relative to locking hole 660) which may inhibit movement of cut guide 600 relative to the bone (i.e., foot 10) attached to the K-wire as depicted in FIG. 10. Further, as depicted in FIG. 10, stem 630 may include a stem locking hole 615 configured (e.g., shaped and dimensioned) to receive a K-wire 2403 therethrough to further inhibit movement between cut guide 600 and the bone portions, (i.e., cuneiform 20 and first metatarsal 30).

As depicted for example in FIG. 10, slots 50 may be formed in cut body 640 between stem 630 and anchoring portion 602. Slots 50 may include a first proximal slot 652, a second proximal slot 654, a first distal slot 656 and a second distal slot 658 configured (e.g., shaped and dimensioned) to receive a saw to allow a cutting and removing of a portion of medial cuneiform 20 and/or first metatarsal 30, for example.

Cut guide 600 may be attached to a bone (e.g., cuneiform 20) via a K-wire (e.g., K-wire 2400) being received in hole 610 such that the K-wire may extend therethrough and may be inserted in the bone. Cut guide 600 may remain attached to a bone (e.g., cuneiform 20) during multiple cuts using a saw (e.g., a saw 170) via slots 650. As depicted in FIG. 9, for example, a cut may be made to a bone (e.g., first metatarsal 30) through first distal slot 656 of slots 650 to remove a portion (e.g., 1.5 mm in a direction parallel relative to axis 32) from the bone or through second distal slot 658 of slots 650 to remove a larger portion (e.g., 3.0 mm) from the bone while a K-wire (e.g., K-wire 2300) is received in opening or anchoring hole 610. In a further example, a cut may be made to a bone (e.g., cuneiform 20) through a first proximal slot 652 of slots 650 to remove a portion (e.g., 1.5 mm in the direction parallel relative to axis 32) from the bone or through second proximal slot 654 of slots 650 to remove a larger portion (e.g., 3.0 mm) from the bone while a K-wire (e.g., K-wire 2400) is received in opening or hole 610.

Further, in an example, cut guide 600 may be pinned on a proximal end thereof (i.e., end 665) by K-wire 2400 received in hole 610 and may be rotated about K-wire 2400 to locate cut guide 600 in differing orientations to provide bone portions having different shapes which may be removed from the space between a metatarsal (e.g., first metatarsal 30) and a cuneiform (e.g., cuneiform 20) to provide a desired aperture or cavity to facilitate a desired realignment of bone (e.g., cuneiform 20 and first metatarsal 30). Cut guide 600 may be used in a similar manner on other portions of a foot or other portion of a body. For example, one or more of slots 650 may thus be utilized to make various cuts at various angles to remove portions of a bone (e.g., of foot 10) as desired to best align bone portions (e.g., cuneiform 20 and first metatarsal 30).

Figure 11:
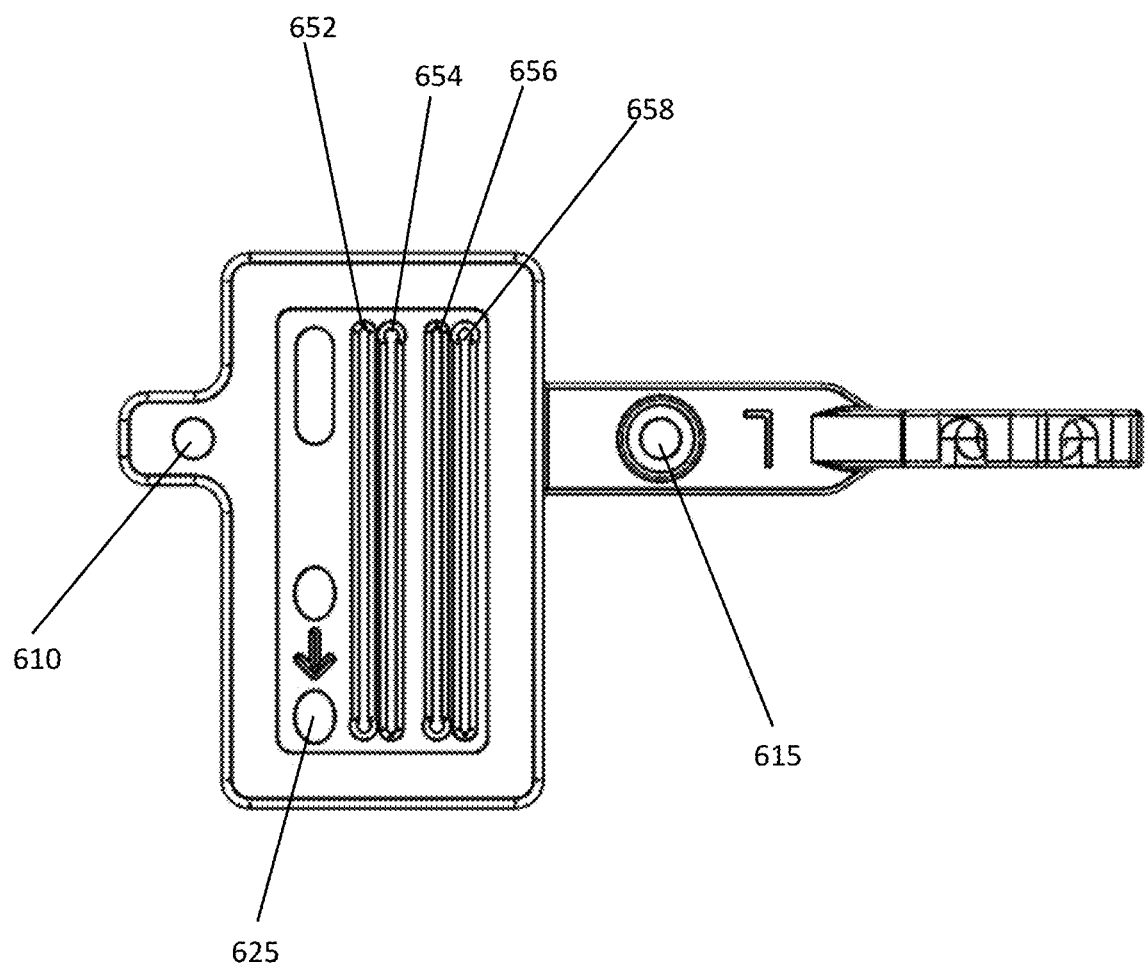
FIG. 11 is a top view of the cut guide of FIG. 6.

FIGS. 10-11 depict cut guide 600 having a stem (e.g., stem 630) and anchoring portion (e.g., anchoring portion 602) offset in a transverse or medial-lateral direction (i.e., bottom to top as depicted in FIG. 11) relative to a central axis in a medial-lateral direction aligned about, or approximately, perpendicular to a longitudinal dimension of body 640 and/or slots 650.

Figure 12:
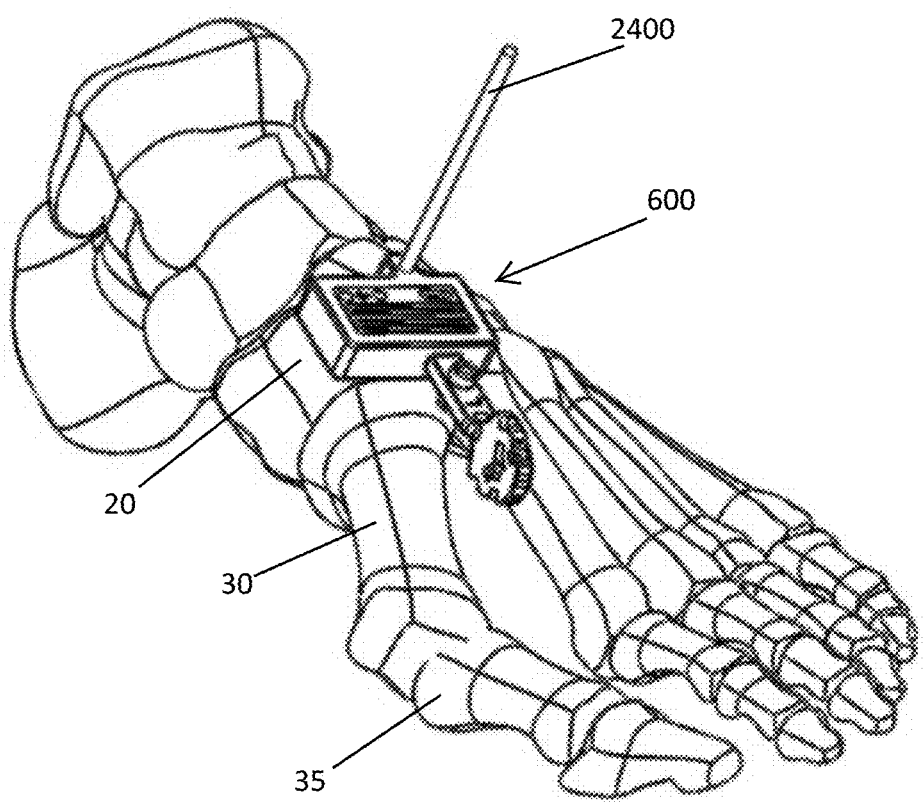
FIG. 12 is a front perspective view of the cut guide received on the K-wire of FIG. 6 with the cut guide rotated toward a desired position of a metatarsal of the foot.
Figure 13:
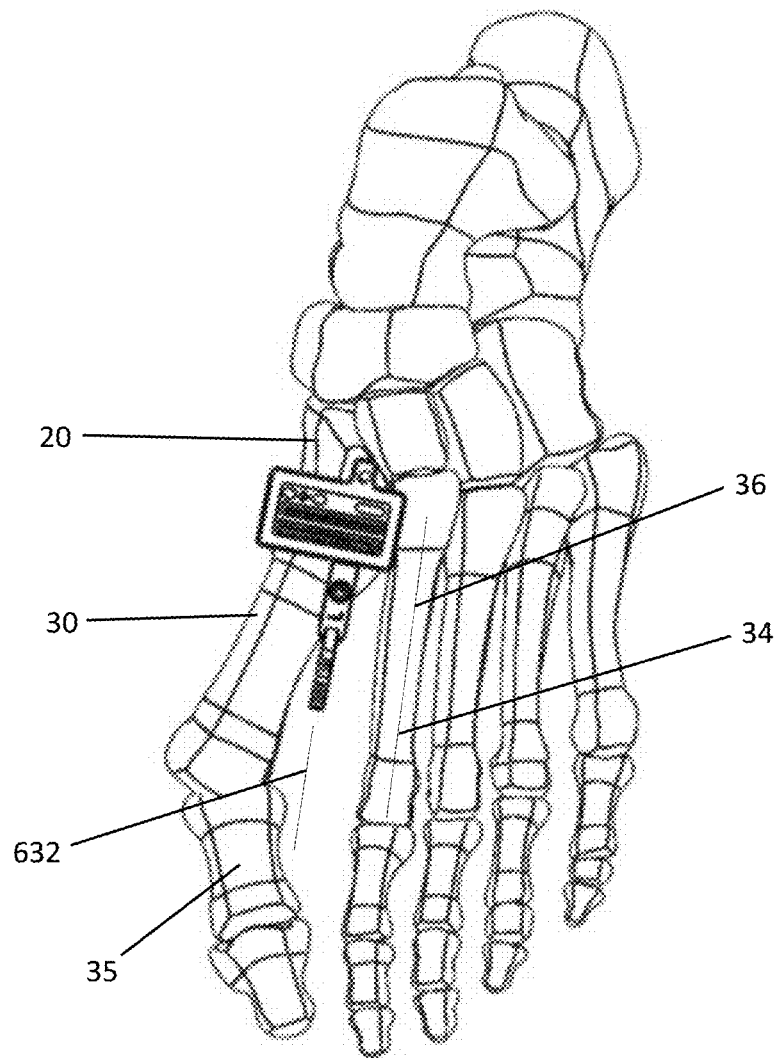
FIG. 13 is a top view of the cut guide and foot of FIG. 12.

As depicted in FIG. 12, K-wire 2405 may be removed from foot 10 and cut guide 600 such that cut guide 600 may be connected to foot 10 only via K-wire 2400. Cut guide 600 may be rotated about K-wire 2400 such that longitudinal axis 632 of stem 630 is aligned with a desired axis of first metatarsal 30 relative to a first proximal phalange 35. As depicted in FIG. 13, longitudinal axis 632 of stem 630 may also be aligned such that longitudinal axis 632 is in a desired position (e.g., parallel, angled at a particular dimension, or otherwise) relative to a longitudinal axis 34 of a second metatarsal 36. For example, longitudinal axis 632 may be aligned parallel to longitudinal axis 34 of second metatarsal 36 such that a cut may be made (e.g., using saw 170 and one of slots 650) perpendicular to a desired axis of first metatarsal 30. Another of slots 650 may be utilized to change (e.g., increase or decrease) an amount of bone resected (e.g., via from a distal portion 21 of medial cuneiform 20 (FIGS. 12-15)). For example, a saw (e.g., saw 170) may be utilized to cut such distal portion from a cuneiform (e.g., medial cuneiform 20).

Figure 14:
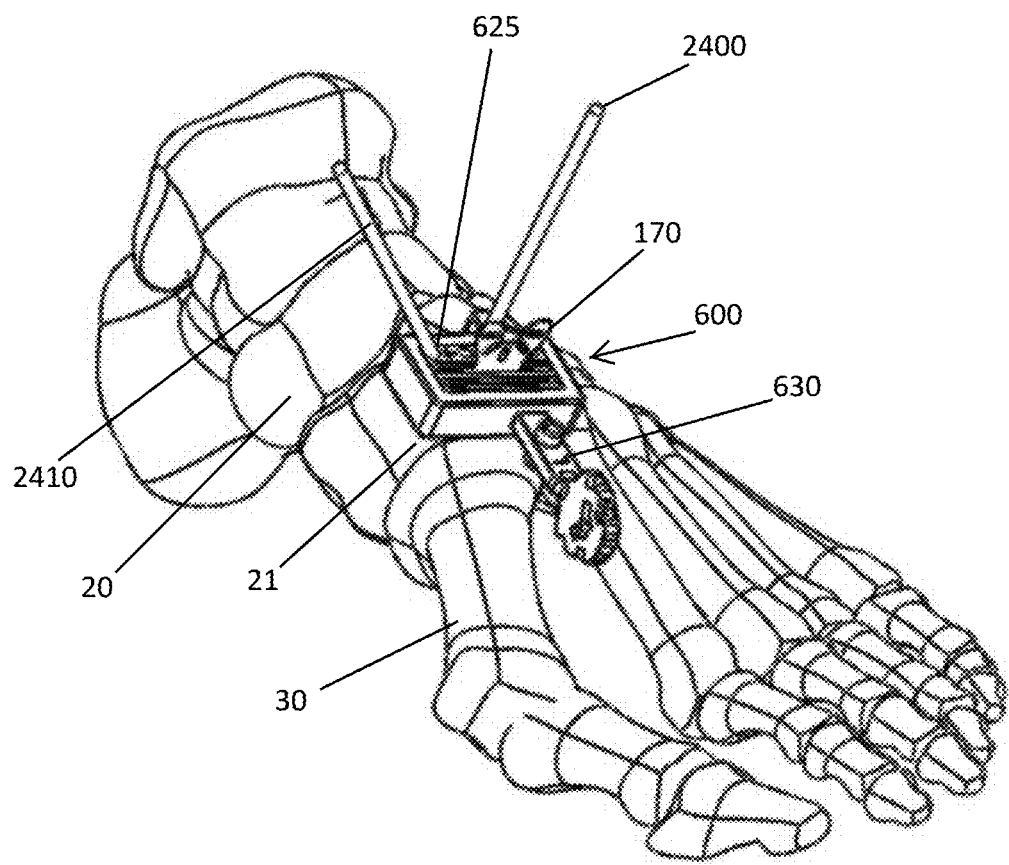
FIG. 14 is a perspective view of the cut guide and foot of FIG. 12 with a K-wire received in a proximal hole of the cut guide and a saw blade received in a proximal slot of the saw guide.

After a desired angle of stem 630 (e.g., axis 632 thereof) relative to axis 34 of second metatarsal 36 is determined (e.g., by a surgeon examining such angle), and an amount of the cuneiform (e.g., medial cuneiform 20) to be removed is determined, and axis 632 is aligned relative to axis 34 as desired, a K-wire 2410 may be inserted through proximal locking hole 625 to secure guide 100 in a desired position. Locking hole 625 may have an axis aligned at a non-perpendicular angle relative to the longitudinal dimension of stem 630 as depicted in FIGS. 10 and 14. For example, a top end of the K-wire 2410 received in locking hole 625 may be located further than a bottom end thereof from distal locking hole 660 at an opposite end of cut guide 600 such that the top portion is angled proximally to securely fasten cut guide 600 relative to first metatarsal 30. After cut guide 600 is attached to foot 10, a saw (e.g., saw 170) may be utilized to cut the cuneiform (e.g., medial cuneiform 20) via second proximal slot 654 of cut guide 100 as depicted in FIG. 14.

Figure 15:
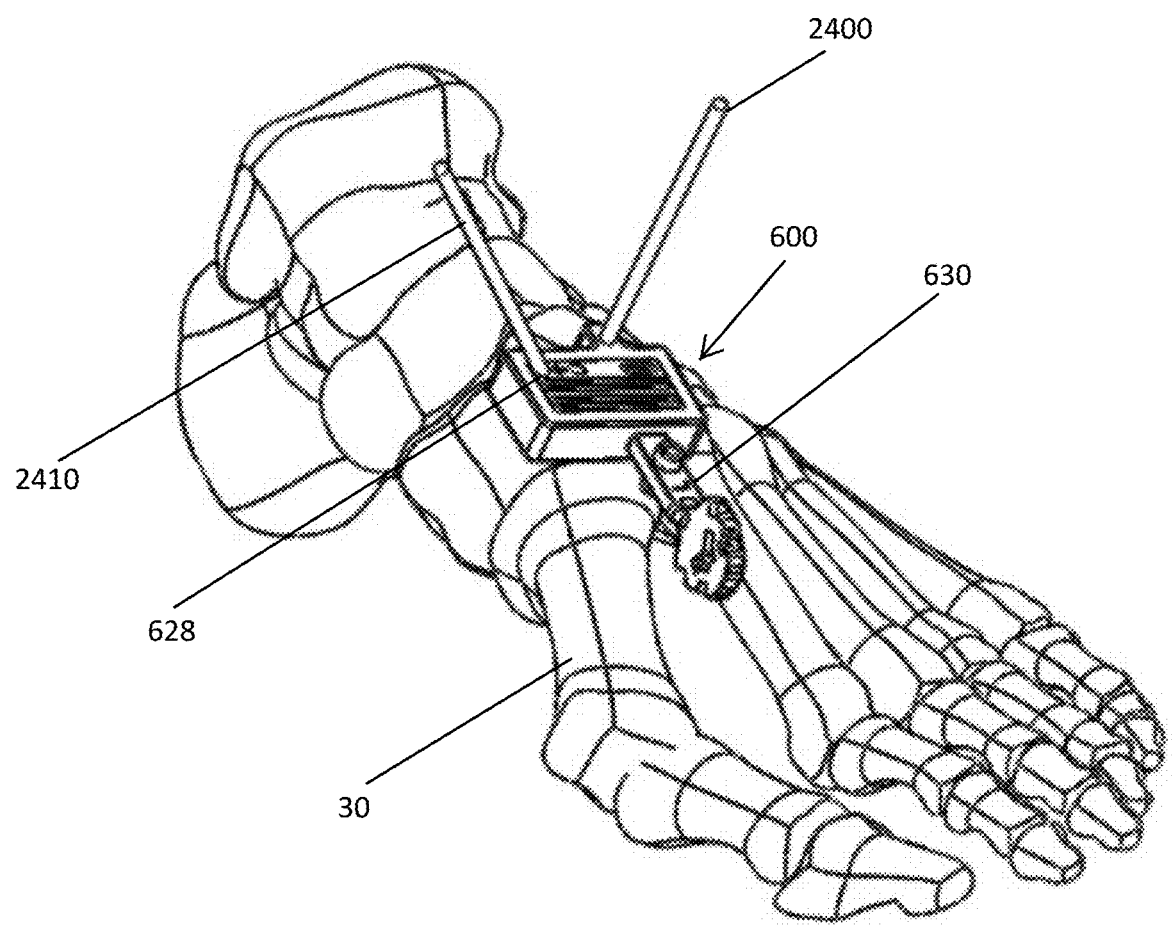
FIG. 15 is a top perspective view of the cut guide and foot of FIG. 14 with the saw blade removed.
Figure 16:
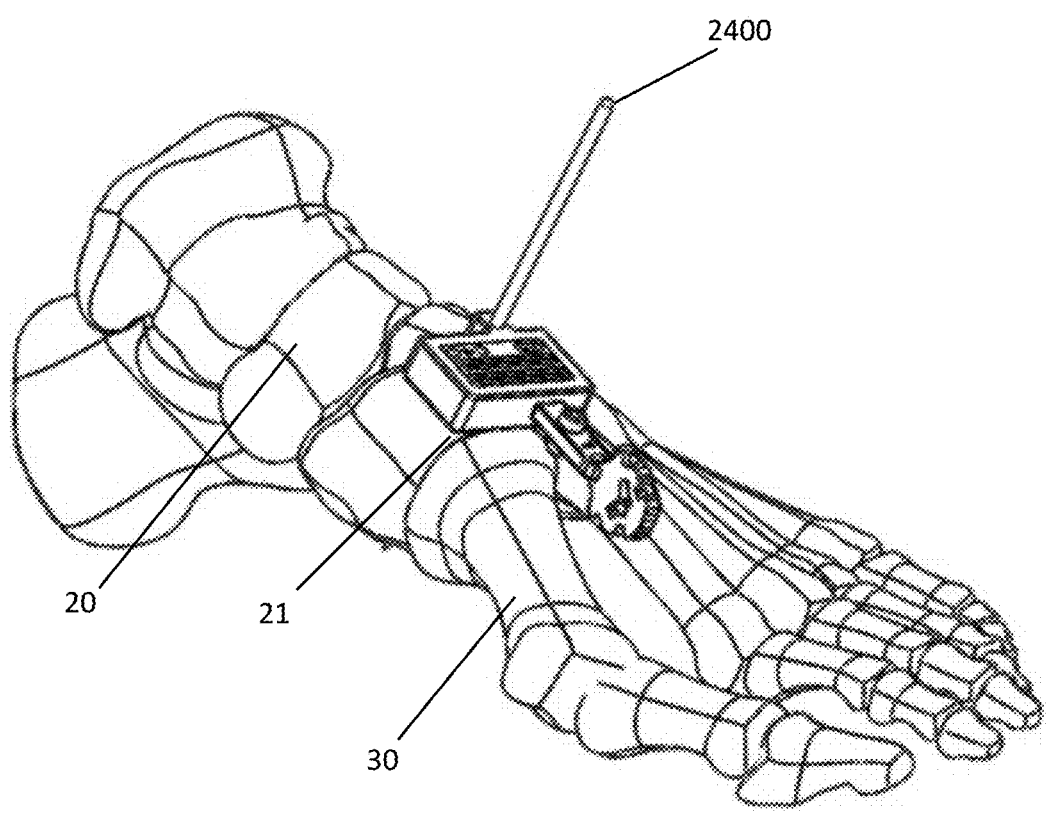
FIG. 16 is a perspective view of the cut guide and foot of FIG. 15 with the K-wire removed from the proximal hole.
Figure 17:
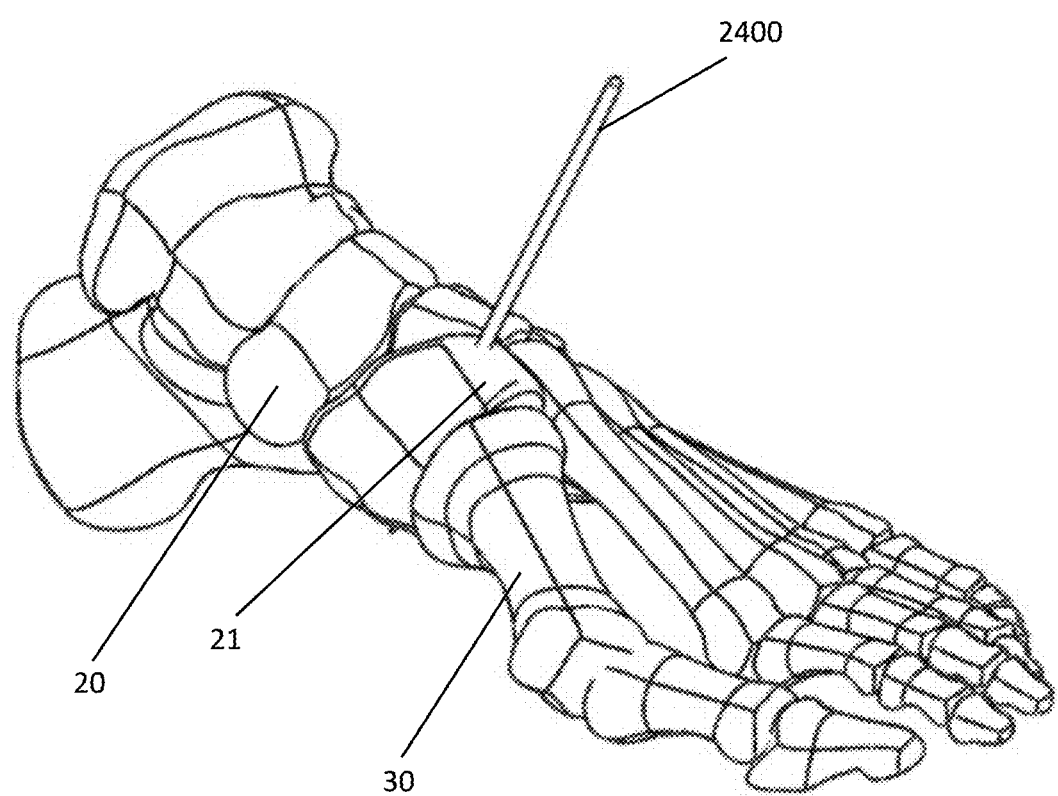
FIG. 17 is a side perspective view of the foot of FIG. 16 with the cut guide removed therefrom.

Saw blade 170 may be removed from cut guide 600 as depicted in FIG. 15 and a K-wire (e.g., K-wire 2410) may be removed from the cut guide (e.g., from proximal locking hole 125) as depicted in FIG. 16. Cut guide 600 may be removed from the remaining K-wire (e.g., K-wire 2400) as depicted in FIG. 17.

Figure 18:
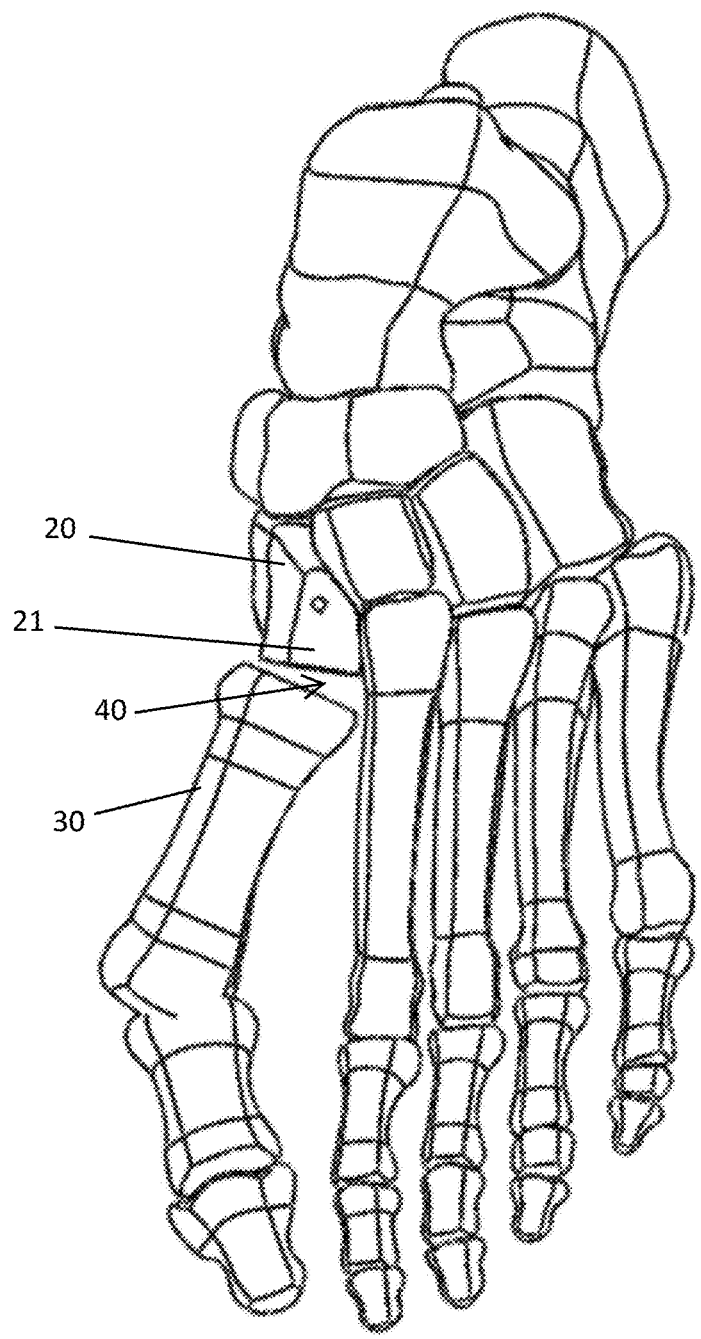
FIG. 18 is a top view of the foot of FIG. 17 showing an aperture created by the cut guide and saw.
Figure 19:
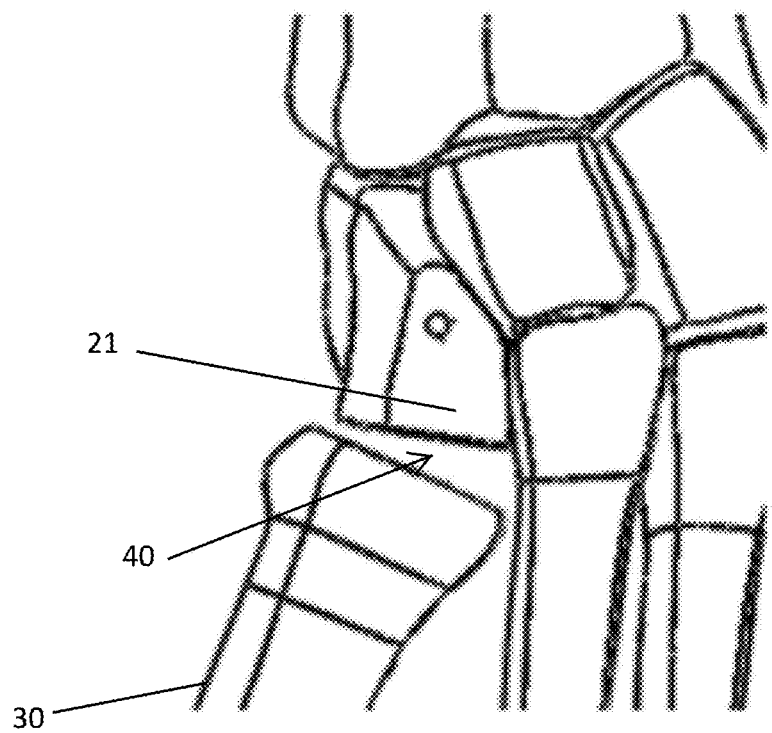
FIG. 19 is a blowup top view of a portion of FIG. 18.
Figure 20:
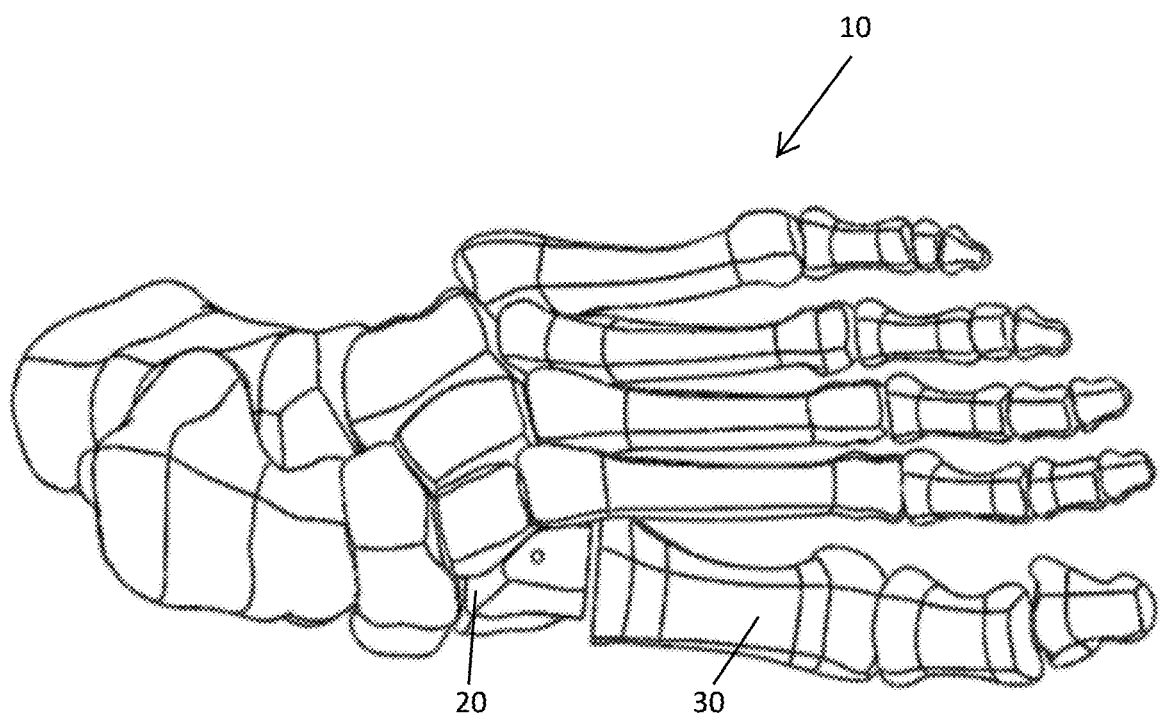
FIG. 20 is a top perspective view of the foot of FIG. 18 with the metatarsal and phalange of the foot manipulated to a desired position.
Figure 21:
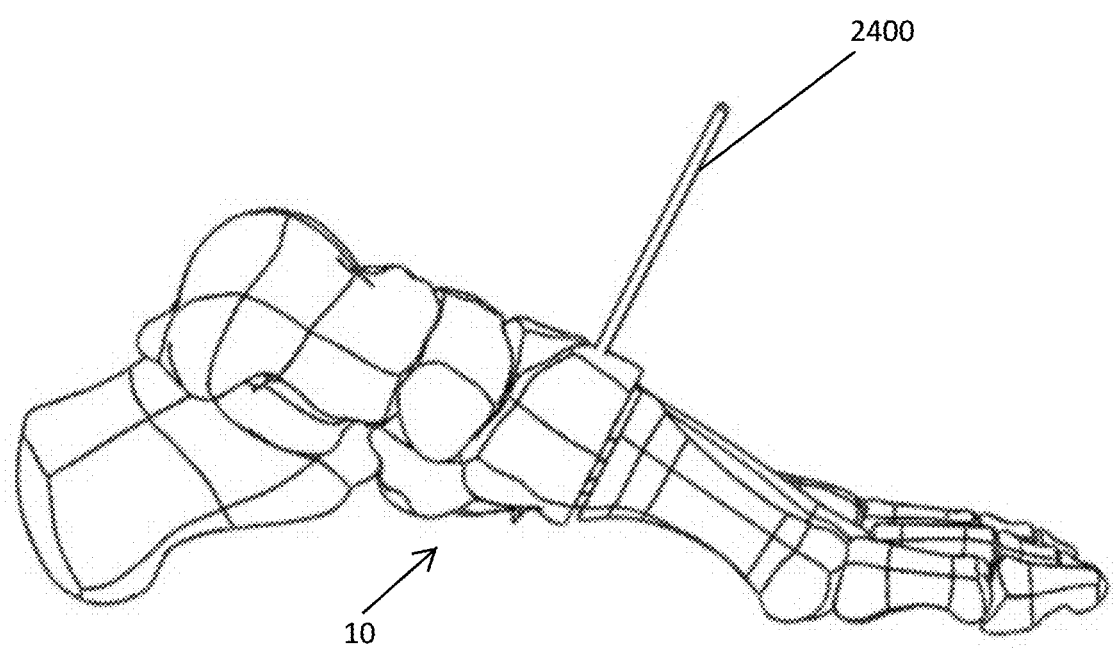
FIG. 21 is a side view of the foot of FIG. 20.
Figure 22:
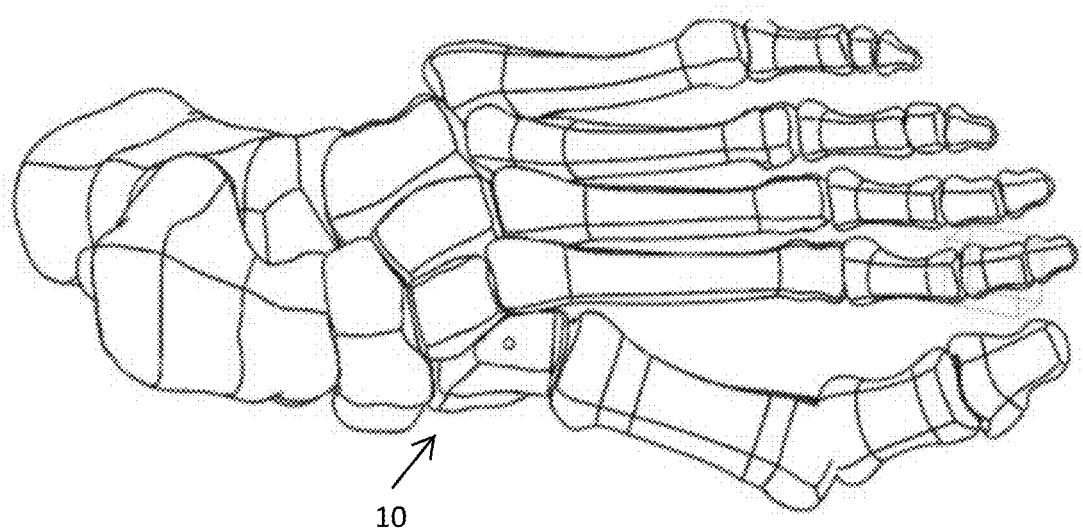
FIG. 22 is a top view of the foot of FIG. 1.
Figure 23:
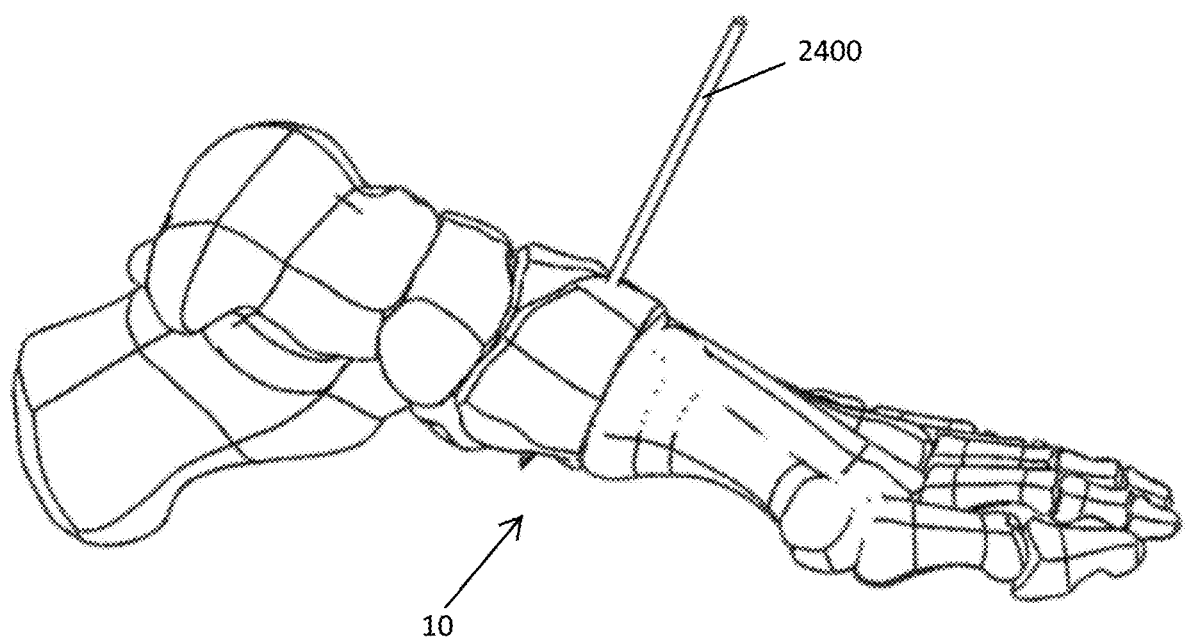
FIG. 23 is a side view of the foot of FIG. 22.
Figure 24:
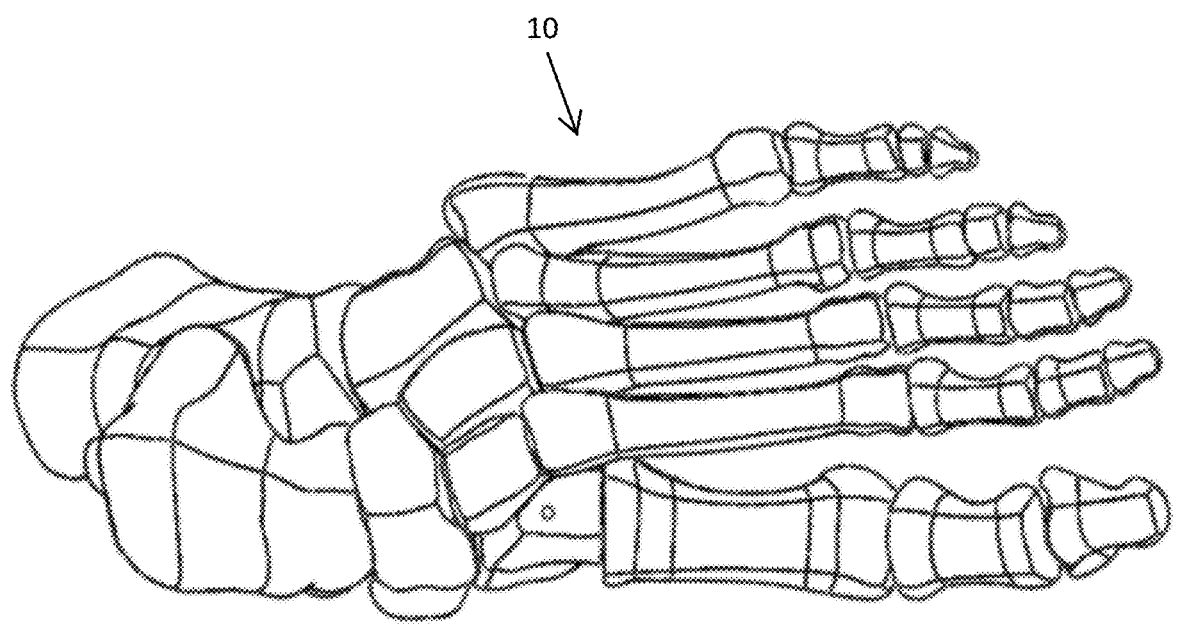
FIG. 24 is a top perspective view of the foot of FIG. 22 after the desired realignment of the metatarsal and phalange of the foot.
Figure 25:
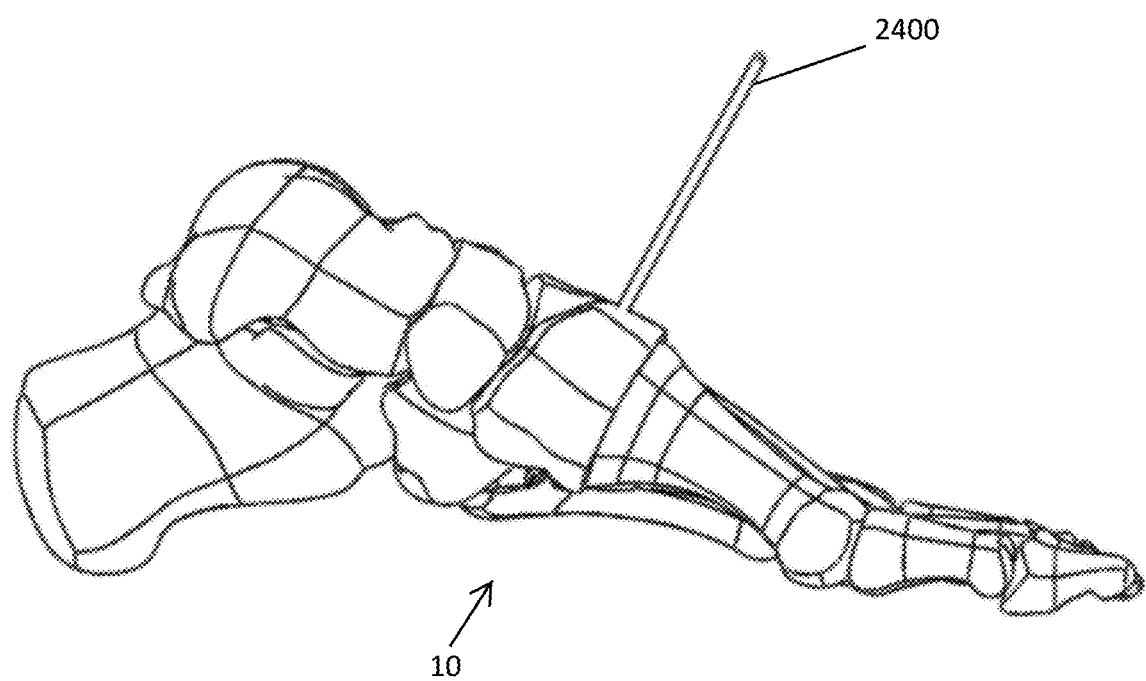
FIG. 25 is a side view of the foot of FIG. 24.

After the cleaning up of the first metatarsal (i.e., first metatarsal 30), i.e., resecting a portion thereof, as described above and cutting the cuneiform (i.e., cuneiform 20) at a desired angle as described above, a space or an aperture 40 (FIGS. 18 and 19) between the bones (e.g., bone portions of foot 10) created by the cutting allows the metatarsal to be manipulated into place (i.e., due to the presence of aperture 40) so that the two cut surfaces (i.e., a distal surface of the cuneiform and proximal surface of the metatarsal) are aligned as depicted in FIGS. 20-21. FIG. 19, which is a blow up of a portion of FIG. 18, depicts a pre-manipulated arrangement of foot 10, including aperture 40. Also, FIGS. 22-23 depict foot 10 prior to the correction described above, while FIGS. 24 and 25 depict foot 10 after such correction.

Figure 32:
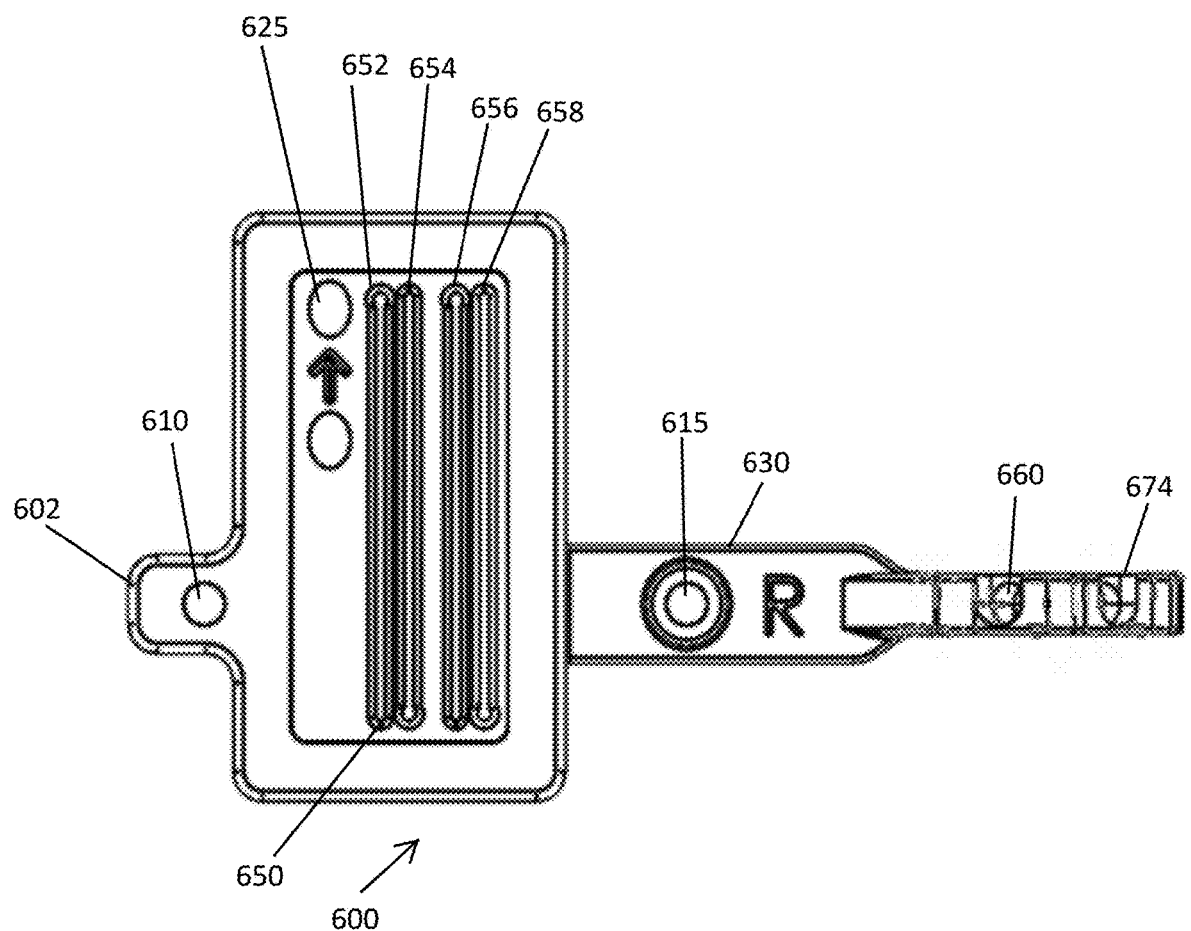
FIG. 32 is a top plan view of the cut guide of FIG. 10 turned upside down.
Figure 33:
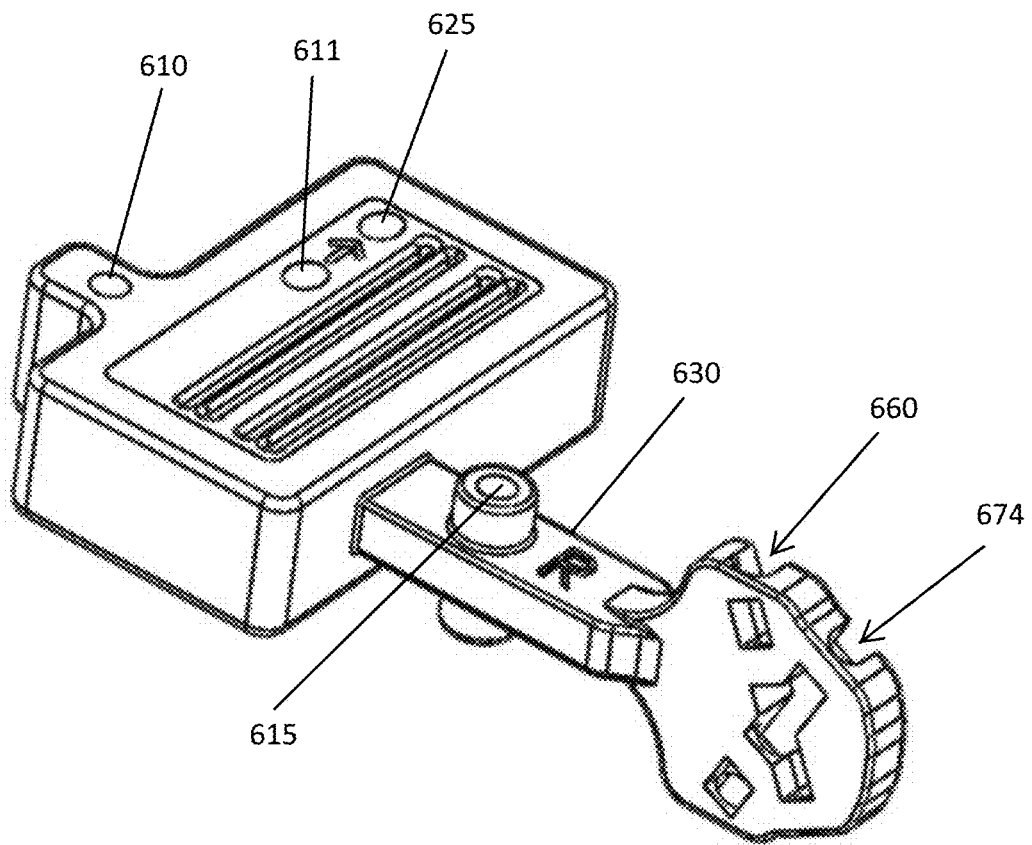
FIG. 33 is a perspective view of the cut guide of FIG. 32.
Figure 34:
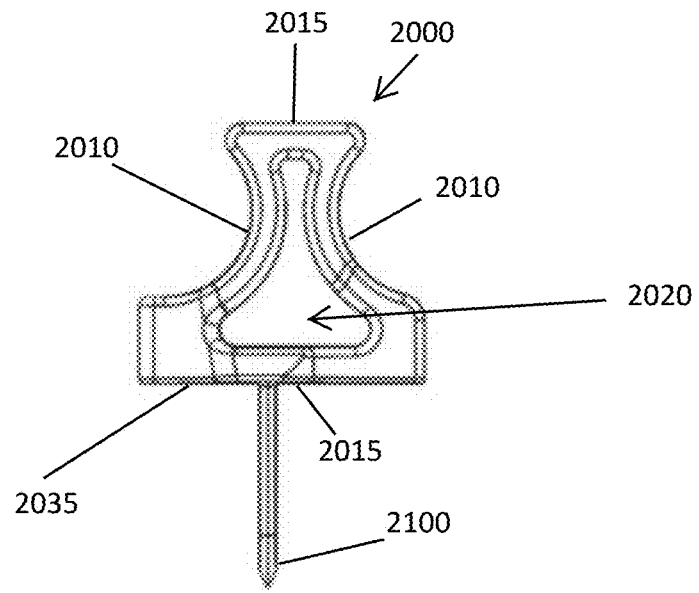
FIG. 34 is a side view of the post drill guide of FIG. 1.
Figure 35:
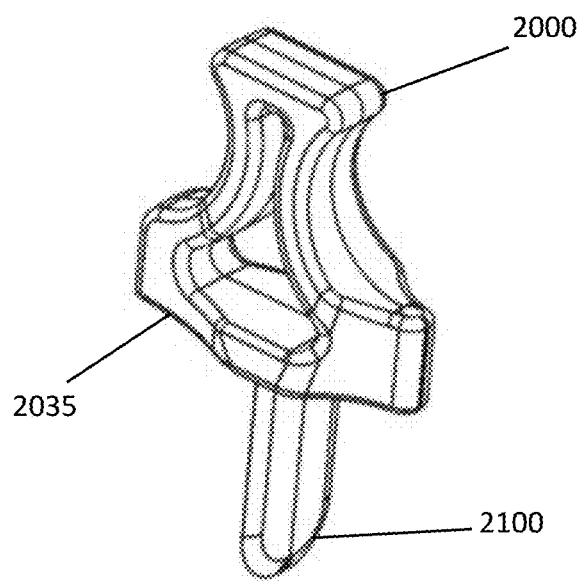
FIG. 35 is a perspective view of the post drill guide of FIG. 1.

FIGS. 32-33 depict a reverse side of cut guide 600 with top and bottom sides reversed. such that cut guide may appear identical to cut guide 600 except that stem 630 and a hole 610 bounded by stem extension 612 may be offset toward a right side of a center of a transverse dimension of cut guide 600 relative to an axis of stem 630 instead of being offset toward a left side thereof. Also, a second distal locking hole 674 of holes 670 may now have an axis angled such that a top end thereof is further from stem extension 612 than a bottom end thereof. A second hole 611 may also be utilized instead of or in addition to hole 610 to receive a K-wire to attach cutting guide 600 to a bone (e.g., foot 10). For example, hole 610 and second hole 611 may have axes oriented proximally and distally opposite to one another such that K-wires received therein may include top and bottom ends located distally and proximally opposite one another relative to anchor portion 602 and/or second distal locking hole 674.

Figure 26:
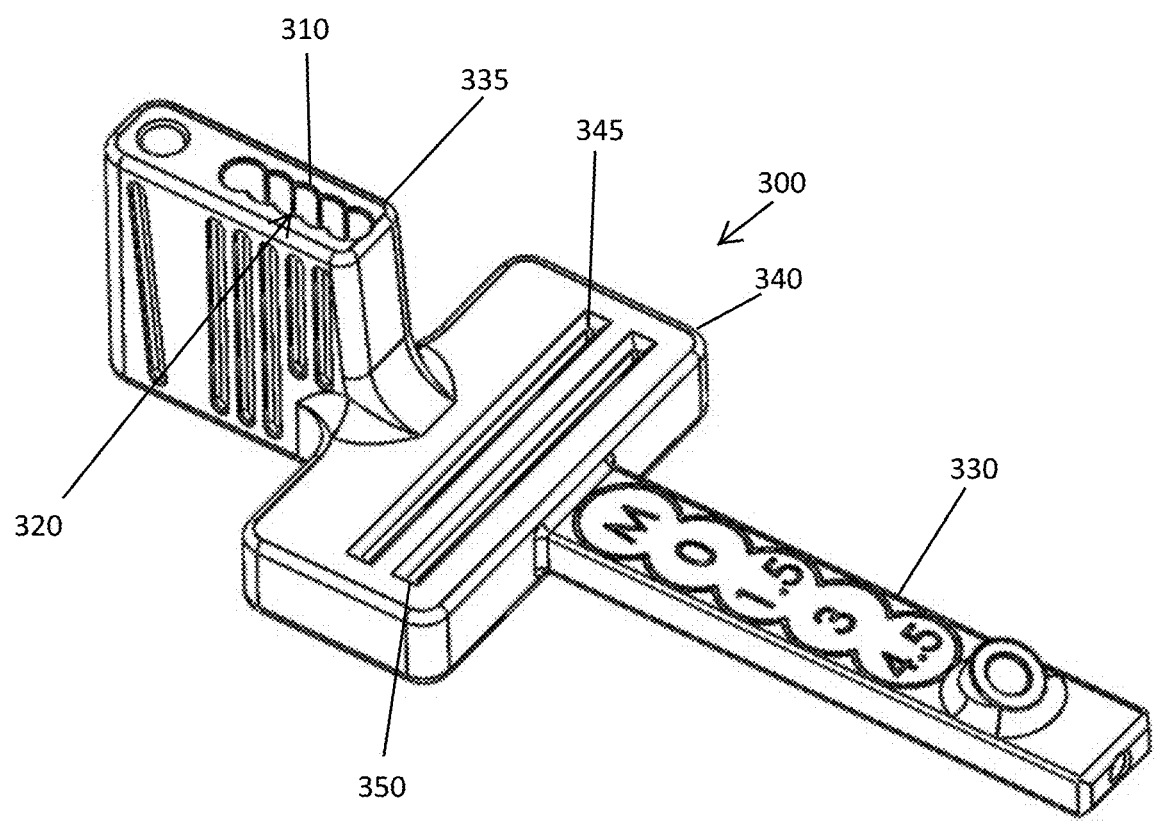
FIG. 26 is a perspective view of an example of a cut guide in accordance with an aspect of the present invention.

In an example, a cut guide 300 is depicted in FIG. 26. In contrast to cut guide 600, cut guide 300 may include a plurality of adjustment holes 320 extending vertically through an anchoring portion 355 of cut guide 300 and configured to receive a K-wire (e.g., K-wire 2400). Cut guide 300 may be placed over K-wire 2400 via a middle opening or hole 310 of adjustment holes 320. A stem 330 of cut guide 300 is connected to a cut body 340 having a first proximal cut slot 345 and a second distal cut slot 350 having longitudinal dimensions extending about or approximately perpendicular to a longitudinal dimension of stem 330.

Cut guide 300 may be located relative to a bone (e.g., foot 10) similarly to cut guide 600 such that a longitudinal dimension or axis thereof is aligned with or extending parallel to axis 32 of first metatarsal 30.

Stem 330 and anchoring portion 335 may extend from a medial-lateral middle portion of a body 340 such the cut guide is symmetric in an axial direction relative to stem 330 and may be utilized as a universal left and right design. More specifically, the symmetric nature of stem 330 and anchoring portion 335 allow cut guide 330 to be flipped over but a longitudinal axis of stem 330 remains centrally located and aligned relative to a central axis of cut guide 300 and about perpendicular to longitudinal dimensions of slots (slot 345 and slot 350) of cut guide 300.

Figure 27:
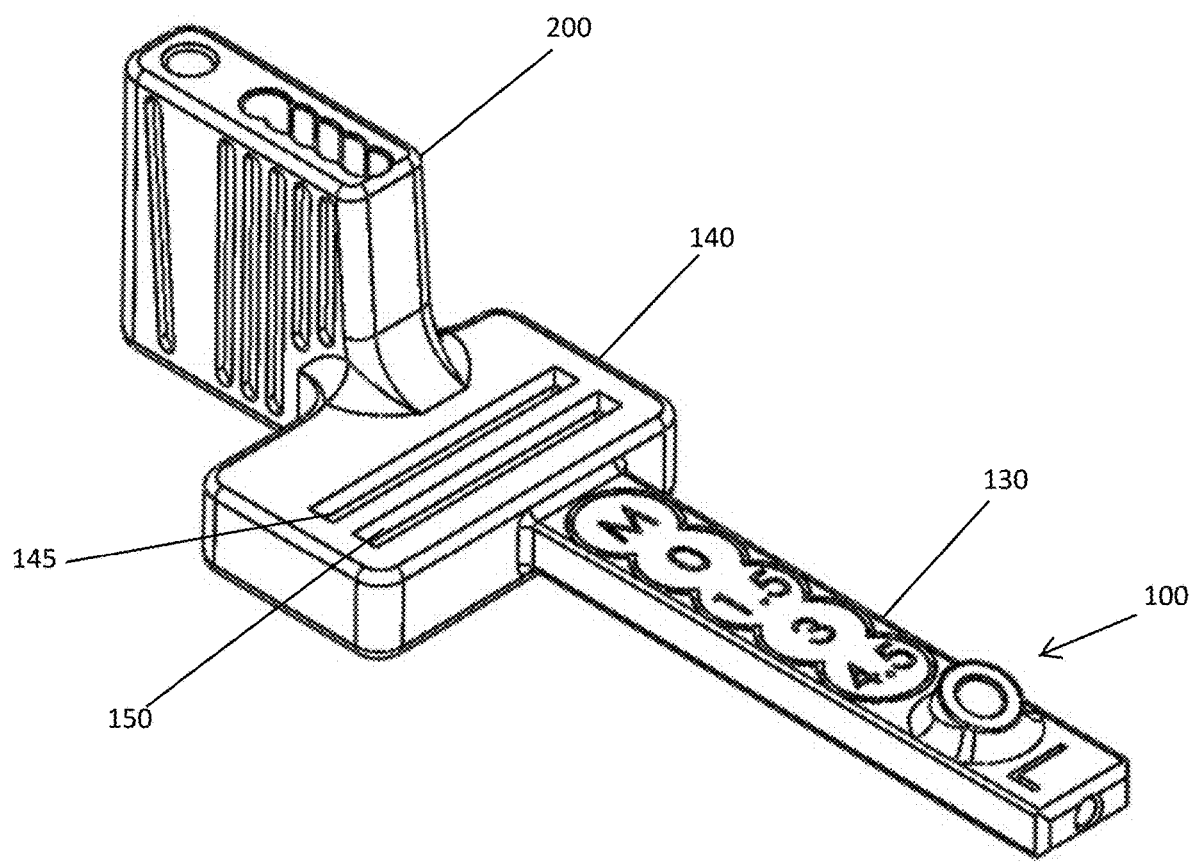
FIG. 27 is a perspective view of another example of a cut guide in accordance with an aspect of the present invention.
Figure 28:
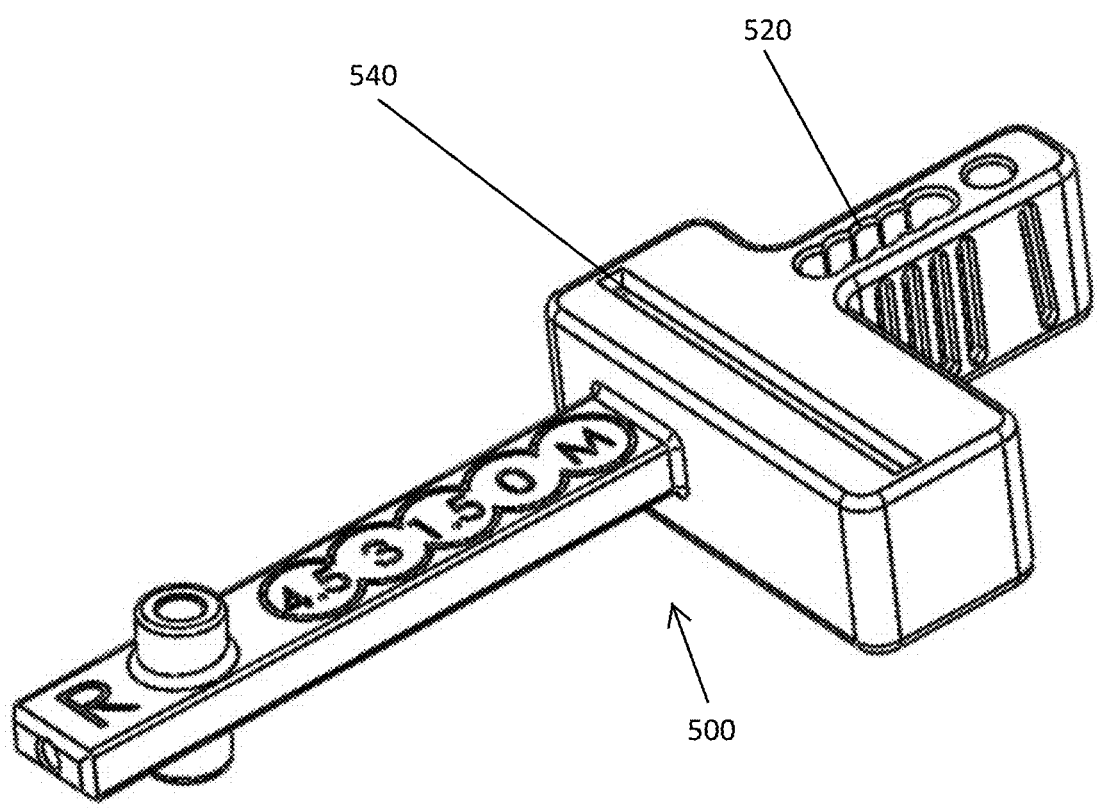
FIG. 28 is a perspective view of a further cut guide in accordance with an aspect of the present invention.
Figure 29:
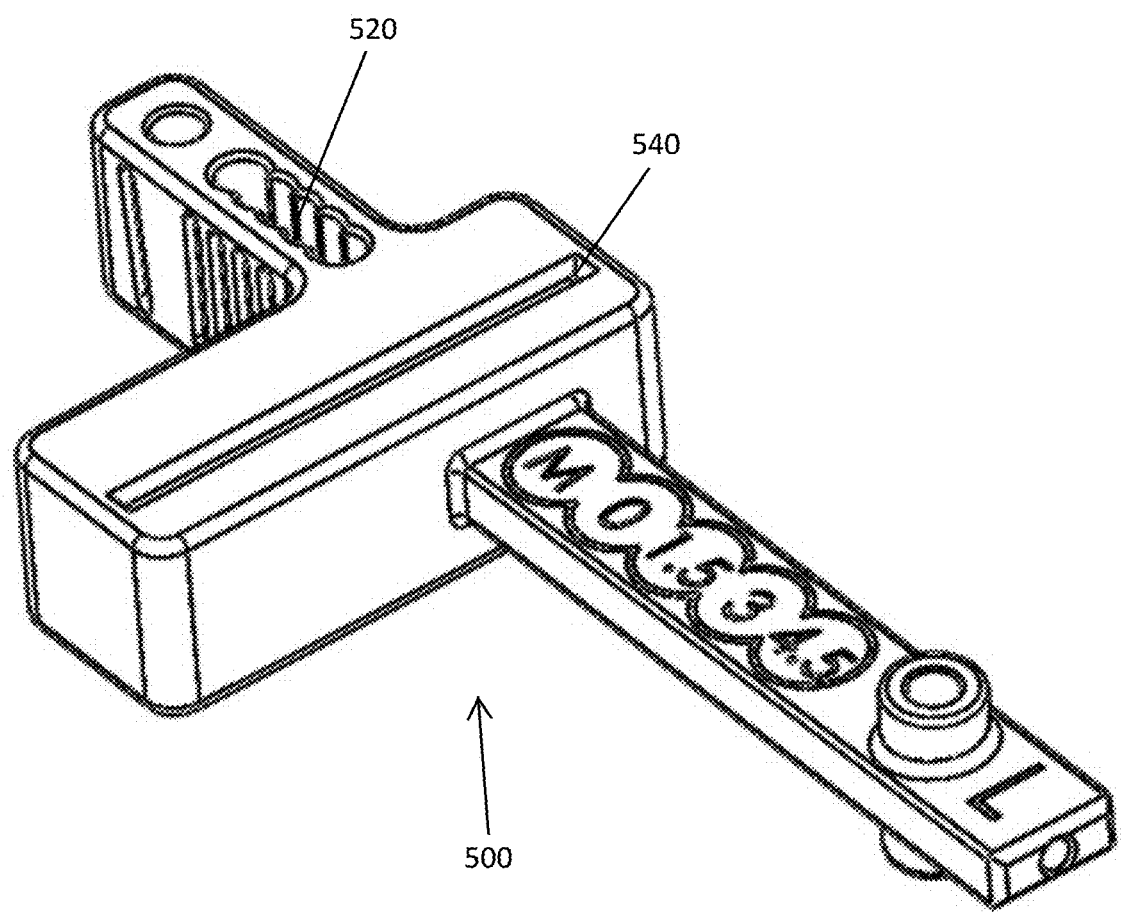
FIG. 29 is a perspective view of the cut guide of FIG. 28 in accordance with an aspect of the present invention.
Figure 30:
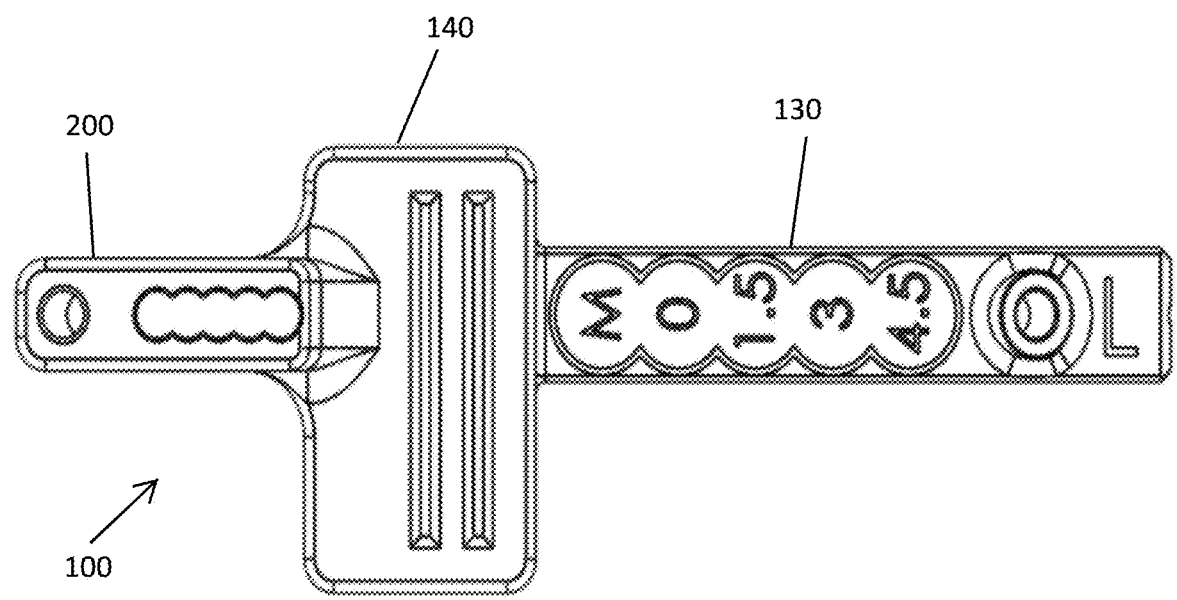
FIG. 30 is a top plan view of the cut guide of FIG. 27.
Figure 31:
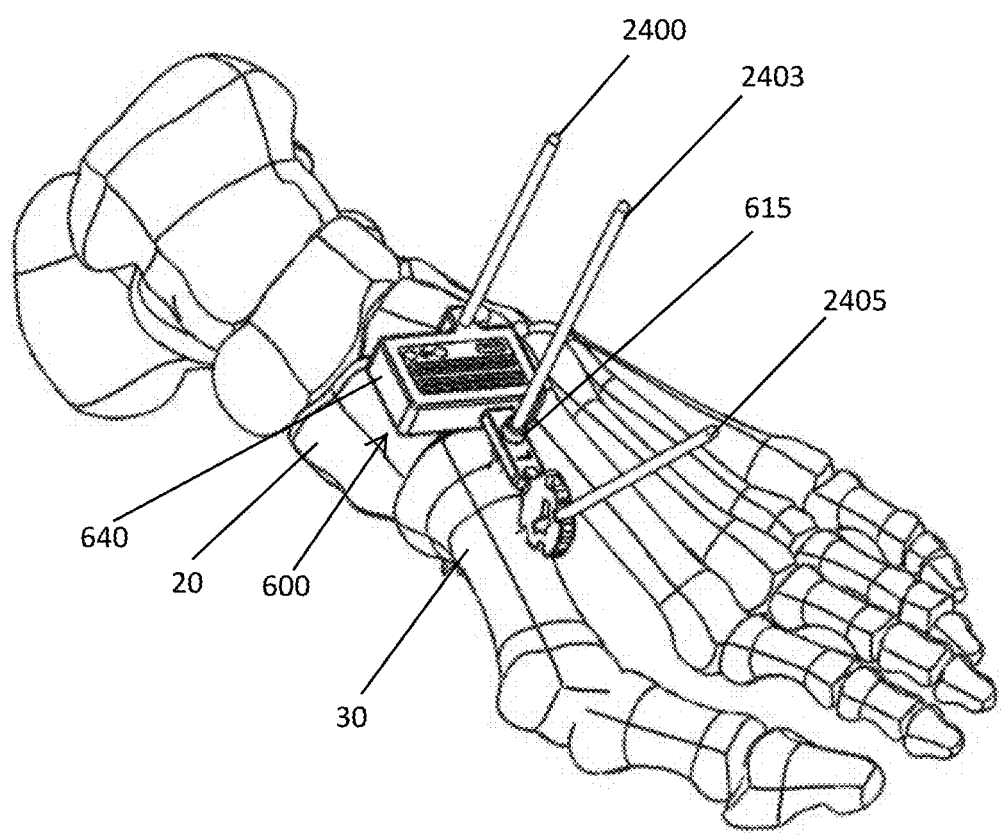
FIG. 31 is a front perspective view of the cut guide of FIG. 8 perspective view of the foot and cut guide of FIG. 8 with a third K-wire received through a middle hole of the cut guide.

As depicted in FIG. 27, a cut guide 100 includes a stem 130 and an anchoring portion 200, which similar to stem 330 and anchoring portion 335, are aligned with each other and offset from a center axis thereof such that different right and left cut guides may be utilized. For example, stem 130 and anchoring portion 200 are offset left of a longitudinal axis of cut guide 100 and a complementary cut guide (not shown) would be offset right of such longitudinal axis. In another example depicted in FIGS. 28-29, a cut guide 500 includes a symmetric universal left and right design where the left cut guide is on the top and right cut guide is on the bottom such that the cut guide may be flipped over from one side to the other depending on the cut desired. Further, cut guide 500 may include a single slot 540 and cut guide may be manipulated such that K-wire 2400 is located among various adjustment holes 520 to longitudinally locate cut guide 500 and slot 540 to allow cuts to be made at various longitudinal locations.

As described above, a cut guide (e.g., cut guide 100, cut guide 300 and cut guide 500) may include several adjustment holes (e.g., holes 320) for receiving K-wires (or other attaching members) to allow the cut guide to be temporarily located or fixed at desired locations (e.g., longitudinal locations along an axis of a metatarsal or desired axis of a rearranged metatarsal) to allow cutting, marking and aligning of metatarsal, phalanges, cuneiform or other portions of a foot. For example, a drilling guide (e.g., guide 2000) and a cut guide (e.g., cut guide 100, cut guide 300, guide 500 and cut guide 600) described above may be utilized to perform a Lapidus procedure. In other examples of cut guides (e.g., cut guide 600), a single anchoring hole (e.g., anchoring hole 610) may be utilized to hold a cut guide relative to a bone (e.g., foot 10) and multiple slots (e.g., slots 650) may be utilized to cut portions of the bone at various increments and at various angles to remove portions thereof to provide a cavity or aperture (e.g., aperture 40) to allow a repositioning of bone portions (e.g., cuneiform 20 and first metatarsal 30).

As described above, a cut guide (e.g., cut guide 100, cut guide 300, cut guide 500, cut guide 600) may include a stem portion (e.g., stem 130, stem 330, stem 530, stem 630) that may be aligned with a desired final alignment of a bone (e.g., a metatarsal) to be manipulated into a final position (e.g., relative to a cuneiform, phalange and/or a remainder of a foot) after the bone and/or an adjacent bone is cut. The cut guide may be aligned with such desired final alignment and secured via a K-wire to the foot such that slots of the cutting guide may be utilized to make cuts (e.g., perpendicularly relative to the desired final alignment) of the bone to allow such desired final alignment to be achieved. The slots (e.g., slot 145, slot 150 of cut guide 100, slots 650 of cut guide 600) may be aligned with longitudinal dimensions substantially perpendicular to the axis (e.g., axis 132) of the cut guide or such slots may be aligned at other desired angles relative to the axis and/or each other as desired relative to cuts to be performed for particular corrective procedures (e.g., the Lapidus procedure).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

We claim:

1. A method for use in aligning bones of a foot, comprising:
    attaching a first portion of a bone cut guide to a first bone by receiving a first wire in a first opening of the first portion of the bone cut guide;
    locating the bone cut guide in a first position relative to the first bone and a second bone and making a first cut of the first bone using a slot of the bone cut guide;
    locating the bone cut guide in a second position relative to the first bone and the second bone and making a second cut of the first bone or the second bone; and
    aligning the first bone with the second bone in a desired final position;
    wherein the bone cut guide comprises a stem having a stem longitudinal axis, the method further comprising attaching the stem to the second bone by receiving a second wire in a stem anchoring opening of the stem and inserting the second wire in the second bone;
    wherein the first portion comprises an anchoring portion having an anchoring portion longitudinal axis, the stem comprises a stem longitudinal axis, the bone cut guide comprises a cut body, and the anchoring portion longitudinal axis is aligned with the stem longitudinal axis, the anchoring portion and the stem connected to the cut body located therebetween, the cut body comprising the slot; and wherein the stem comprises an elongated portion and a distal portion located distal to the elongated portion, the distal portion projecting upwardly and downwardly from the elongated portion.

2. The method of claim 1 wherein said stem longitudinal axis is offset transversely relative to a central axis perpendicular to a slot longitudinal dimension of said slot located at a transverse center of said slot longitudinal dimension.

3. The method of claim 1 wherein said stem longitudinal axis is aligned with a central axis perpendicular to a body longitudinal dimension of said cut body located at a transverse center of said body longitudinal dimension.

4. The method of claim 1 wherein the slot has a slot longitudinal axis aligned about perpendicularly to a longitudinal axis of the bone cut guide.

5. The method of claim 1 wherein the making the second cut comprises making the second cut in a second slot of the bone cut guide, the second slot having a second slot longitudinal axis aligned about parallel to the slot and located distal to the slot.

6. The method of claim 1 further comprising receiving a second wire in a second opening of the anchoring portion to connect the anchoring portion to the first bone to inhibit a rotation of the anchoring portion about the first wire.

7. The method of claim 1 wherein the making the second cut comprises making the second cut in the slot.

8. The method of claim 1 wherein the making the second cut comprises making the second cut in a second slot of the cut body, the second slot distal to the first slot.

* * * * *